US010296717B2

(12) United States Patent
Isaacs

(10) Patent No.: US 10,296,717 B2
(45) Date of Patent: May 21, 2019

(54) AUTOMATED PRESCRIPTION WORKFLOW FOR DEVICE MANAGEMENT

(71) Applicant: salesforce.com, inc., San Francisco, CA (US)

(72) Inventor: Charlie Isaacs, San Jose, CA (US)

(73) Assignee: salesforce.com, inc., San Francisco, CA (US)

( * ) Notice: Subject to any disclaimer, the term of this patent is extended or adjusted under 35 U.S.C. 154(b) by 906 days.

(21) Appl. No.: 14/712,435

(22) Filed: May 14, 2015

(65) Prior Publication Data
US 2016/0335414 A1    Nov. 17, 2016

(51) Int. Cl.
| G06F 11/00 | (2006.01) |
| G06F 19/00 | (2018.01) |
| G06F 11/07 | (2006.01) |
| G16H 20/60 | (2018.01) |
| G06N 5/02 | (2006.01) |

(52) U.S. Cl.
CPC ........ G06F 19/3456 (2013.01); G06F 11/079 (2013.01); G06F 11/0766 (2013.01); G06F 11/0793 (2013.01); *G06N 5/022* (2013.01); *G16H 20/60* (2018.01)

(58) Field of Classification Search
CPC ............ G06F 11/0751; G06F 11/0766; G06F 11/0775; G06F 11/0778; G06F 11/0784; G06F 11/0787; G06F 11/079; G06F 11/0793
See application file for complete search history.

(56) References Cited

U.S. PATENT DOCUMENTS

| 5,577,188 A | 11/1996 | Zhu |
| 5,608,872 A | 3/1997 | Schwartz et al. |
| 5,649,104 A | 7/1997 | Carleton et al. |
| 5,715,450 A | 2/1998 | Ambrose et al. |
| 5,761,419 A | 6/1998 | Schwartz et al. |
| 5,819,038 A | 10/1998 | Carleton et al. |
| 5,821,937 A | 10/1998 | Tonelli et al. |

(Continued)

OTHER PUBLICATIONS

"Google Plus Users", Google+Ripples, Oct. 31, 2011 [retrieved on Feb. 21, 2012 from Internet at http://www.googleplusers.com/google-ripples.html], 3 pages.

*Primary Examiner* — Michael Maskulinski
(74) *Attorney, Agent, or Firm* — Weaver Austin Villeneuve & Sampson LLP

(57) ABSTRACT

Disclosed are some examples of systems, apparatus, methods and storage media for automated device management, and more specifically, for detecting exceptions in devices and facilitating workflows to resolve the exceptions. In one innovative aspect, a database system is configurable to maintain at least one knowledge database storing a plurality of prescriptions, each prescription defining a respective action-oriented workflow for one or more exceptions. The system is further configurable to receive device data associated with the devices, analyze the received device data, and detect occurrences of exceptions based on the analysis. The system is further configurable to determine whether the knowledge base includes a prescription for a detected exception, and responsive to a determination that the knowledge base includes a prescription for the detected exception, trigger a first workflow for remedying the detected exception based on the prescription.

20 Claims, 12 Drawing Sheets

(56) References Cited

U.S. PATENT DOCUMENTS

| | | | |
|---|---|---|---|
| 5,831,610 | A | 11/1998 | Tonelli et al. |
| 5,873,096 | A | 2/1999 | Lim et al. |
| 5,918,159 | A | 6/1999 | Fomukong et al. |
| 5,963,953 | A | 10/1999 | Cram et al. |
| 5,983,227 | A | 11/1999 | Nazem et al. |
| 6,092,083 | A | 7/2000 | Brodersen et al. |
| 6,161,149 | A | 12/2000 | Achacoso et al. |
| 6,169,534 | B1 | 1/2001 | Raffel et al. |
| 6,178,425 | B1 | 1/2001 | Brodersen et al. |
| 6,189,011 | B1 | 2/2001 | Lim et al. |
| 6,216,133 | B1 | 4/2001 | Masthoff |
| 6,216,135 | B1 | 4/2001 | Brodersen et al. |
| 6,233,617 | B1 | 5/2001 | Rothwein et al. |
| 6,236,978 | B1 | 5/2001 | Tuzhilin |
| 6,266,669 | B1 | 7/2001 | Brodersen et al. |
| 6,288,717 | B1 | 9/2001 | Dunkle |
| 6,295,530 | B1 | 9/2001 | Ritchie et al. |
| 6,324,568 | B1 | 11/2001 | Diec et al. |
| 6,324,693 | B1 | 11/2001 | Brodersen et al. |
| 6,336,137 | B1 | 1/2002 | Lee et al. |
| D454,139 | S | 3/2002 | Feldcamp et al. |
| 6,367,077 | B1 | 4/2002 | Brodersen et al. |
| 6,393,605 | B1 | 5/2002 | Loomans |
| 6,405,220 | B1 | 6/2002 | Brodersen et al. |
| 6,411,949 | B1 | 6/2002 | Schaffer |
| 6,434,550 | B1 | 8/2002 | Warner et al. |
| 6,446,089 | B1 | 9/2002 | Brodersen et al. |
| 6,535,909 | B1 | 3/2003 | Rust |
| 6,549,908 | B1 | 4/2003 | Loomans |
| 6,553,563 | B2 | 4/2003 | Ambrose et al. |
| 6,560,461 | B1 | 5/2003 | Fomukong et al. |
| 6,574,635 | B2 | 6/2003 | Stauber et al. |
| 6,577,726 | B1 | 6/2003 | Huang et al. |
| 6,601,087 | B1 | 7/2003 | Zhu et al. |
| 6,604,117 | B2 | 8/2003 | Lim et al. |
| 6,604,128 | B2 | 8/2003 | Diec et al. |
| 6,609,150 | B2 | 8/2003 | Lee et al. |
| 6,621,834 | B1 | 9/2003 | Scherpbier et al. |
| 6,654,032 | B1 | 11/2003 | Zhu et al. |
| 6,665,648 | B2 | 12/2003 | Brodersen et al. |
| 6,665,655 | B1 | 12/2003 | Warner et al. |
| 6,684,438 | B2 | 2/2004 | Brodersen et al. |
| 6,711,565 | B1 | 3/2004 | Subramaniam et al. |
| 6,724,399 | B1 | 4/2004 | Katchour et al. |
| 6,728,702 | B1 | 4/2004 | Subramaniam et al. |
| 6,728,960 | B1 | 4/2004 | Loomans et al. |
| 6,732,095 | B1 | 5/2004 | Warshavsky et al. |
| 6,732,100 | B1 | 5/2004 | Brodersen et al. |
| 6,732,111 | B2 | 5/2004 | Brodersen et al. |
| 6,742,141 | B1 * | 5/2004 | Miller ................ G06F 11/0748 706/45 |
| 6,754,681 | B2 | 6/2004 | Brodersen et al. |
| 6,763,351 | B1 | 7/2004 | Subramaniam et al. |
| 6,763,501 | B1 | 7/2004 | Zhu et al. |
| 6,768,904 | B2 | 7/2004 | Kim |
| 6,772,229 | B1 | 8/2004 | Achacoso et al. |
| 6,782,383 | B2 | 8/2004 | Subramaniam et al. |
| 6,804,330 | B1 | 10/2004 | Jones et al. |
| 6,826,565 | B2 | 11/2004 | Ritchie et al. |
| 6,826,582 | B1 | 11/2004 | Chatterjee et al. |
| 6,826,745 | B2 | 11/2004 | Coker |
| 6,829,655 | B1 | 12/2004 | Huang et al. |
| 6,842,748 | B1 | 1/2005 | Warner et al. |
| 6,850,895 | B2 | 2/2005 | Brodersen et al. |
| 6,850,949 | B2 | 2/2005 | Warner et al. |
| 6,907,566 | B1 | 6/2005 | McElfresh et al. |
| 7,058,860 | B2 * | 6/2006 | Miller ................ G06F 11/0727 714/47.3 |
| 7,062,502 | B1 | 6/2006 | Kesler |
| 7,069,231 | B1 | 6/2006 | Cinarkaya et al. |
| 7,069,497 | B1 | 6/2006 | Desai |
| 7,100,111 | B2 | 8/2006 | McElfresh et al. |
| 7,181,758 | B1 | 2/2007 | Chan |
| 7,269,590 | B2 | 9/2007 | Hull et al. |
| 7,289,976 | B2 | 10/2007 | Kihneman et al. |
| 7,340,411 | B2 | 3/2008 | Cook |
| 7,356,482 | B2 | 4/2008 | Frankland et al. |
| 7,373,599 | B2 | 5/2008 | McElfresh et al. |
| 7,401,094 | B1 | 7/2008 | Kesler |
| 7,406,501 | B2 | 7/2008 | Szeto et al. |
| 7,412,455 | B2 | 8/2008 | Dillon |
| 7,454,509 | B2 | 11/2008 | Boulter et al. |
| 7,508,789 | B2 | 3/2009 | Chan |
| 7,599,935 | B2 | 10/2009 | La Rotonda et al. |
| 7,603,331 | B2 | 10/2009 | Tuzhilin et al. |
| 7,603,483 | B2 | 10/2009 | Psounis et al. |
| 7,620,655 | B2 | 11/2009 | Larsson et al. |
| 7,644,122 | B2 | 1/2010 | Weyer et al. |
| 7,668,861 | B2 | 2/2010 | Steven |
| 7,698,160 | B2 | 4/2010 | Beaven et al. |
| 7,730,478 | B2 | 6/2010 | Weissman |
| 7,747,648 | B1 | 6/2010 | Kraft et al. |
| 7,779,039 | B2 | 8/2010 | Weissman et al. |
| 7,779,475 | B2 | 8/2010 | Jakobson et al. |
| 7,827,208 | B2 | 11/2010 | Bosworth et al. |
| 7,853,881 | B1 | 12/2010 | Aly Assal et al. |
| 7,945,653 | B2 | 5/2011 | Zukerberg et al. |
| 8,005,896 | B2 | 8/2011 | Cheah |
| 8,014,943 | B2 | 9/2011 | Jakobson |
| 8,015,495 | B2 | 9/2011 | Achacoso et al. |
| 8,032,297 | B2 | 10/2011 | Jakobson |
| 8,073,850 | B1 | 12/2011 | Hubbard et al. |
| 8,082,301 | B2 | 12/2011 | Ahlgren et al. |
| 8,095,413 | B1 | 1/2012 | Beaven |
| 8,095,531 | B2 | 1/2012 | Weissman et al. |
| 8,095,594 | B2 | 1/2012 | Beaven et al. |
| 8,103,611 | B2 | 1/2012 | Tuzhilin et al. |
| 8,150,913 | B2 | 4/2012 | Cheah |
| 8,209,308 | B2 | 6/2012 | Rueben et al. |
| 8,209,333 | B2 | 6/2012 | Hubbard et al. |
| 8,275,836 | B2 | 9/2012 | Beaven et al. |
| 8,457,545 | B2 | 6/2013 | Chan |
| 8,484,111 | B2 | 7/2013 | Frankland et al. |
| 8,490,025 | B2 | 7/2013 | Jakobson et al. |
| 8,504,945 | B2 | 8/2013 | Jakobson et al. |
| 8,510,045 | B2 | 8/2013 | Rueben et al. |
| 8,510,664 | B2 | 8/2013 | Rueben et al. |
| 8,566,301 | B2 | 10/2013 | Rueben et al. |
| 8,646,103 | B2 | 2/2014 | Jakobson et al. |
| 9,183,072 | B1 * | 11/2015 | Makuch ............. G06F 11/0709 |
| 9,229,800 | B2 * | 1/2016 | Jain ........................ G06Q 30/01 |
| 9,864,673 | B2 * | 1/2018 | Michel ............... G06F 11/3664 |
| 2001/0044791 | A1 | 11/2001 | Richter et al. |
| 2002/0072951 | A1 | 6/2002 | Lee et al. |
| 2002/0082892 | A1 | 6/2002 | Raffel et al. |
| 2002/0129352 | A1 | 9/2002 | Brodersen et al. |
| 2002/0140731 | A1 | 10/2002 | Subramaniam et al. |
| 2002/0143997 | A1 | 10/2002 | Huang et al. |
| 2002/0162090 | A1 | 10/2002 | Parnell et al. |
| 2002/0165742 | A1 | 11/2002 | Robbins |
| 2003/0004971 | A1 | 1/2003 | Gong |
| 2003/0018705 | A1 | 1/2003 | Chen et al. |
| 2003/0018830 | A1 | 1/2003 | Chen et al. |
| 2003/0056140 | A1 * | 3/2003 | Taylor ................ G06F 11/0709 714/4.1 |
| 2003/0066031 | A1 | 4/2003 | Laane et al. |
| 2003/0066032 | A1 | 4/2003 | Ramachandran et al. |
| 2003/0069936 | A1 | 4/2003 | Warner et al. |
| 2003/0070000 | A1 | 4/2003 | Coker et al. |
| 2003/0070004 | A1 | 4/2003 | Mukundan et al. |
| 2003/0070005 | A1 | 4/2003 | Mukundan et al. |
| 2003/0074418 | A1 | 4/2003 | Coker et al. |
| 2003/0120675 | A1 | 6/2003 | Stauber et al. |
| 2003/0151633 | A1 | 8/2003 | George et al. |
| 2003/0159136 | A1 | 8/2003 | Huang et al. |
| 2003/0187921 | A1 | 10/2003 | Diec et al. |
| 2003/0189600 | A1 | 10/2003 | Gune et al. |
| 2003/0204427 | A1 | 10/2003 | Gune et al. |
| 2003/0206192 | A1 | 11/2003 | Chen et al. |
| 2003/0225730 | A1 | 12/2003 | Warner et al. |
| 2004/0001092 | A1 | 1/2004 | Rothwein et al. |
| 2004/0010489 | A1 | 1/2004 | Rio et al. |
| 2004/0015981 | A1 | 1/2004 | Coker et al. |
| 2004/0027388 | A1 | 2/2004 | Berg et al. |

(56) References Cited

U.S. PATENT DOCUMENTS

| | | |
|---|---|---|
| 2004/0128001 A1 | 7/2004 | Levin et al. |
| 2004/0186860 A1 | 9/2004 | Lee et al. |
| 2004/0193510 A1 | 9/2004 | Catahan et al. |
| 2004/0199489 A1 | 10/2004 | Barnes-Leon et al. |
| 2004/0199536 A1 | 10/2004 | Barnes-Leon et al. |
| 2004/0199543 A1 | 10/2004 | Braud et al. |
| 2004/0249854 A1 | 12/2004 | Barnes-Leon et al. |
| 2004/0260534 A1 | 12/2004 | Pak et al. |
| 2004/0260659 A1 | 12/2004 | Chan et al. |
| 2004/0268299 A1 | 12/2004 | Lei et al. |
| 2005/0050555 A1 | 3/2005 | Exley et al. |
| 2005/0091098 A1 | 4/2005 | Brodersen et al. |
| 2006/0136869 A1* | 6/2006 | Lamm ............... G06F 11/0748 717/109 |
| 2008/0249972 A1 | 10/2008 | Dillon |
| 2009/0063415 A1 | 3/2009 | Chatfield et al. |
| 2009/0100342 A1 | 4/2009 | Jakobson |
| 2009/0177744 A1 | 7/2009 | Marlow et al. |
| 2011/0107137 A1* | 5/2011 | Lam ................... G06F 11/0748 714/4.4 |
| 2011/0154123 A1* | 6/2011 | Barrall .............. G06F 11/0727 714/42 |
| 2011/0218958 A1 | 9/2011 | Warshavsky et al. |
| 2011/0247051 A1 | 10/2011 | Bulumulla et al. |
| 2011/0260879 A1* | 10/2011 | Avner ................ G06F 11/0748 340/679 |
| 2012/0042218 A1 | 2/2012 | Cinarkaya et al. |
| 2012/0233137 A1 | 9/2012 | Jakobson et al. |
| 2012/0290407 A1 | 11/2012 | Hubbard et al. |
| 2013/0007527 A1* | 1/2013 | Petukhov ........... G06F 11/0793 714/37 |
| 2013/0212497 A1 | 8/2013 | Zelenko et al. |
| 2013/0218948 A1 | 8/2013 | Jakobson |
| 2013/0218949 A1 | 8/2013 | Jakobson |
| 2013/0218966 A1 | 8/2013 | Jakobson |
| 2013/0247216 A1 | 9/2013 | Cinarkaya et al. |
| 2014/0129536 A1* | 5/2014 | Anand ............... G06Q 10/0635 707/706 |
| 2014/0359537 A1 | 12/2014 | Jakobson et al. |
| 2015/0006289 A1 | 1/2015 | Jakobson et al. |
| 2015/0007050 A1 | 1/2015 | Jakobson et al. |
| 2015/0095162 A1 | 4/2015 | Jakobson et al. |
| 2015/0142596 A1 | 5/2015 | Jakobson et al. |
| 2015/0172563 A1 | 6/2015 | Jakobson et al. |
| 2016/0103856 A1 | 4/2016 | Isaacs |
| 2016/0224401 A1* | 8/2016 | Adinarayan ......... G06F 11/079 |
| 2016/0274961 A1* | 9/2016 | Thomas ............. G06F 11/0709 |
| 2016/0274962 A1* | 9/2016 | Fortune ............... G06F 11/079 |

* cited by examiner

AUTOMATED PRESCRIPTION WORKFLOW FOR DEVICE MANAGEMENT

COPYRIGHT NOTICE

A portion of the disclosure of this patent document contains material which is subject to copyright protection. The copyright owner has no objection to the facsimile reproduction by anyone of the patent document or the patent disclosure, as it appears in the United States Patent and Trademark Office patent file or records, but otherwise reserves all copyright rights whatsoever.

TECHNICAL FIELD

This patent document relates generally to device management, and more specifically, to action-oriented prescription workflows for automating device management.

BACKGROUND

"Cloud computing" services provide shared resources, software, and information to computers and other devices upon request or on demand. Cloud computing typically involves the over-the-Internet provision of dynamically-scalable and often virtualized resources. Technological details can be abstracted from end-users, who no longer have need for expertise in, or control over, the technology infrastructure "in the cloud" that supports them. In cloud computing environments, software applications can be accessible over the Internet rather than installed locally on personal or in-house computer systems. Some of the applications or on-demand services provided to end-users can include the ability for a user to create, view, modify, store and share documents and other files.

BRIEF DESCRIPTION OF THE DRAWINGS

The included drawings are for illustrative purposes and serve to provide examples of possible structures and operations for the disclosed inventive systems, apparatus, methods and computer-readable storage media. These drawings in no way limit any changes in form and detail that may be made by one skilled in the art without departing from the spirit and scope of the disclosed implementations.

DETAILED DESCRIPTION

Figure 1A:
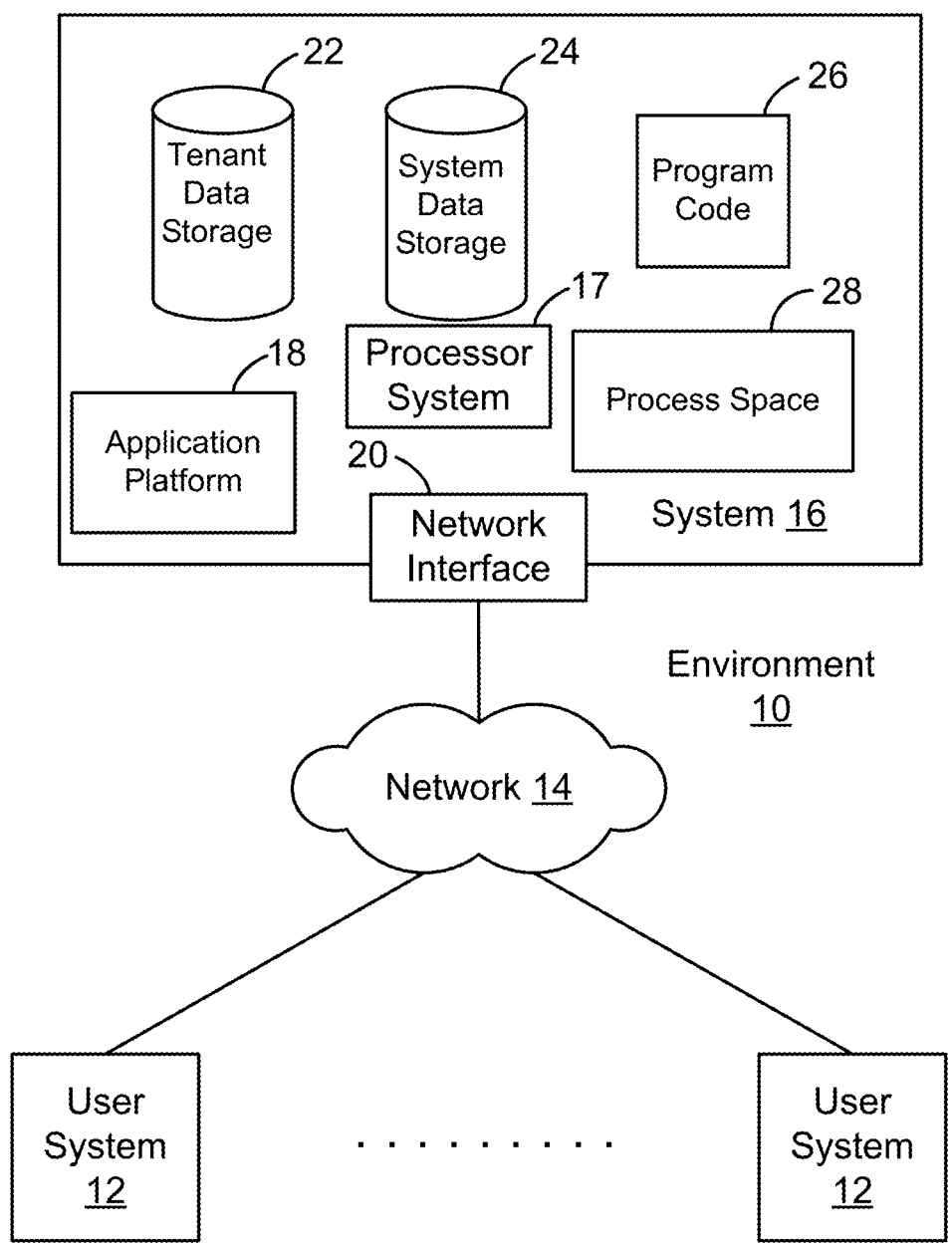
FIG. 1A shows a block diagram of an example environment in which an on-demand database service can be used according to some implementations.

Examples of systems, apparatus, computer-readable storage media, and methods according to the disclosed implementations are described in this section. These examples are being provided solely to add context and aid in the understanding of the disclosed implementations. It will thus be apparent to one skilled in the art that the disclosed implementations may be practiced without some or all of the specific details provided. In other instances, certain process or method operations, also referred to herein as "blocks," have not been described in detail in order to avoid unnecessarily obscuring the disclosed implementations. Other implementations and applications also are possible, and as such, the following examples should not be taken as definitive or limiting either in scope or setting.

In the following detailed description, references are made to the accompanying drawings, which form a part of the description and in which are shown, by way of illustration, specific implementations. Although these disclosed implementations are described in sufficient detail to enable one skilled in the art to practice the implementations, it is to be understood that these examples are not limiting, such that other implementations may be used and changes may be made to the disclosed implementations without departing from their spirit and scope. For example, the blocks of the methods shown and described herein are not necessarily performed in the order indicated in some other implementations. Additionally, in some other implementations, the disclosed methods may include more or fewer blocks than are described. As another example, some blocks described herein as separate blocks may be combined in some other implementations. Conversely, what may be described herein as a single block may be implemented in multiple blocks in some other implementations. Additionally, the conjunction "or" is intended herein in the inclusive sense where appropriate unless otherwise indicated; for example, the phrase "A, B or C" is intended to include the possibilities of "A," "B," "C," "A and B," "B and C," "A and C" and "A, B and C."

Various implementations described and referenced herein are directed to database systems, computer-implemented methods and computer-readable storage media for detecting and resolving exceptions, anomalies or problems encountered in or generated by devices, or experienced by users operating devices. Various implementations relate generally to automated device management. In one innovative aspect, a device management system is configured to trigger and facilitate workflows to resolve exceptions detected in various devices managed by the device management system. The device management system maintains a prescription database storing prescriptions that define associated workflows for resolving particular exceptions. In some implementations, each prescription more particularly defines a respective action-oriented workflow including one or more automated steps for carrying out the prescription and resolving the exception. In some implementations, the device management system is generally configurable to receive device data associated with devices deployed by one or more organizations or by one or more enterprises or users associated with an organization. The device management system is further configurable to analyze the received device data and to detect the occurrences of exceptions based on the analysis. Responsive to the detection of an exception, the device management system determines whether the prescription database includes a prescription for the detected exception. Responsive to a determination that the prescription database includes a prescription, the device management system triggers a workflow defined by the prescription to resolve the exception. In some implementations, the workflow includes updating software or firmware installed in the device. In some implementations, the device management system is further configurable to trigger a second workflow in response to a determination that the prescription database does not include a prescription for the detected exception. In some such implementations, a prescription can then be generated by or in conjunction with the device management system based on analysis of the steps performed in the second workflow leading to the resolution of the exception.

In some implementations, the customers, employees or other users described herein are users (or "members") of an interactive online "enterprise social network," also referred to herein as a "social networking system," an "enterprise social networking system," an "enterprise collaborative network," or more simply as an "enterprise network." Such online enterprise networks are increasingly becoming a common way to facilitate communication among people, any of whom can be recognized as enterprise users. One example of an online enterprise social network is Chatter®, provided by salesforce.com, inc. of San Francisco, Calif. salesforce.com, inc. is a provider of enterprise social networking services, customer relationship management (CRM) services and other database management services, any of which can be accessed and used in conjunction with the techniques disclosed herein in some implementations. These various services can be provided in a cloud computing environment as described herein, for example, in the context of a multi-tenant database system. Some of the described techniques or processes can be implemented without having to install software locally, that is, on computing devices of users interacting with services available through the cloud. While the disclosed implementations may be described with reference to Chatter® and more generally to enterprise social networking, those of ordinary skill in the art should understand that the disclosed techniques are neither limited to Chatter® nor to any other services and systems provided by salesforce.com, inc. and can be implemented in the context of various other database systems such as cloud-based systems that are not part of a multi-tenant database system or which do not provide enterprise social networking services.

I. Example System Overview

FIG. 1A shows a block diagram of an example of an environment 10 in which an on-demand database service can be used in accordance with some implementations. The environment 10 includes user systems 12, a network 14, a database system 16 (also referred to herein as a "cloud-based system"), a processor system 17, an application platform 18, a network interface 20, tenant database 22 for storing tenant data 23, system database 24 for storing system data 25, program code 26 for implementing various functions of the system 16, and process space 28 for executing database system processes and tenant-specific processes, such as running applications as part of an application hosting service. In some other implementations, environment 10 may not have all of these components or systems, or may have other components or systems instead of, or in addition to, those listed above.

In some implementations, the environment 10 is an environment in which an on-demand database service exists. An on-demand database service, such as that which can be implemented using the system 16, is a service that is made available to users outside of the enterprise(s) that own, maintain or provide access to the system 16. As described above, such users generally do not need to be concerned with building or maintaining the system 16. Instead, resources provided by the system 16 may be available for such users' use when the users need services provided by the system 16; that is, on the demand of the users. Some on-demand database services can store information from one or more tenants into tables of a common database image to form a multi-tenant database system (MTS). The term "multi-tenant database system" can refer to those systems in which various elements of hardware and software of a database system may be shared by one or more customers or tenants. For example, a given application server may simultaneously process requests for a great number of customers, and a given database table may store rows of data such as feed items for a potentially much greater number of customers. A database image can include one or more database objects. A relational database management system (RDBMS) or the equivalent can execute storage and retrieval of information against the database object(s).

Application platform 18 can be a framework that allows the applications of system 16 to execute, such as the hardware or software infrastructure of the system 16. In some implementations, the application platform 18 enables the creation, management and execution of one or more applications developed by the provider of the on-demand database service, users accessing the on-demand database service via user systems 12, or third party application developers accessing the on-demand database service via user systems 12.

In some implementations, the system 16 implements a web-based customer relationship management (CRM) system. For example, in some such implementations, the system 16 includes application servers configured to implement and execute CRM software applications as well as provide related data, code, forms, renderable web pages and documents and other information to and from user systems 12 and to store to, and retrieve from, a database system related data, objects, and Web page content. In some MTS implementations, data for multiple tenants may be stored in the same physical database object in tenant database 22. In some such implementations, tenant data is arranged in the storage medium(s) of tenant database 22 so that data of one tenant is kept logically separate from that of other tenants so that one tenant does not have access to another tenant's data, unless such data is expressly shared. The system 16 also implements applications other than, or in addition to, a CRM application. For example, the system 16 can provide tenant access to multiple hosted (standard and custom) applications, including a CRM application. User (or third party developer) applications, which may or may not include CRM, may be supported by the application platform 18. The application platform 18 manages the creation and storage of the applications into one or more database objects and the execution of the applications in one or more virtual machines in the process space of the system 16.

According to some implementations, each system 16 is configured to provide web pages, forms, applications, data and media content to user (client) systems 12 to support the access by user systems 12 as tenants of system 16. As such, system 16 provides security mechanisms to keep each tenant's data separate unless the data is shared. If more than one MTS is used, they may be located in close proximity to one another (for example, in a server farm located in a single building or campus), or they may be distributed at locations remote from one another (for example, one or more servers located in city A and one or more servers located in city B). As used herein, each MTS could include one or more logically or physically connected servers distributed locally or across one or more geographic locations. Additionally, the term "server" is meant to refer to a computing device or system, including processing hardware and process space(s), an associated storage medium such as a memory device or database, and, in some instances, a database application (for example, OODBMS or RDBMS) as is well known in the art. It should also be understood that "server system" and "server" are often used interchangeably herein. Similarly, the database objects described herein can be implemented as part of a single database, a distributed database, a collection of distributed databases, a database with redundant online or offline backups or other redundancies, etc., and can include a distributed database or storage network and associated processing intelligence.

The network 14 can be or include any network or combination of networks of systems or devices that communicate with one another. For example, the network 14 can be or include any one or any combination of a LAN (local area network), WAN (wide area network), telephone network, wireless network, cellular network, point-to-point network, star network, token ring network, hub network, or other appropriate configuration. The network 14 can include a TCP/IP (Transfer Control Protocol and Internet Protocol) network, such as the global internetwork of networks often referred to as the "Internet" (with a capital "I"). The Internet will be used in many of the examples herein. However, it should be understood that the networks that the disclosed implementations can use are not so limited, although TCP/IP is a frequently implemented protocol.

The user systems 12 can communicate with system 16 using TCP/IP and, at a higher network level, other common Internet protocols to communicate, such as HTTP, FTP, AFS, WAP, etc. In an example where HTTP is used, each user system 12 can include an HTTP client commonly referred to as a "web browser" or simply a "browser" for sending and receiving HTTP signals to and from an HTTP server of the system 16. Such an HTTP server can be implemented as the sole network interface 20 between the system 16 and the network 14, but other techniques can be used in addition to or instead of these techniques. In some implementations, the network interface 20 between the system 16 and the network 14 includes load sharing functionality, such as round-robin HTTP request distributors to balance loads and distribute incoming HTTP requests evenly over a number of servers. In MTS implementations, each of the servers can have access to the MTS data; however, other alternative configurations may be used instead.

The user systems 12 can be implemented as any computing device(s) or other data processing apparatus or systems usable by users to access the database system 16. For example, any of user systems 12 can be a desktop computer, a work station, a laptop computer, a tablet computer, a handheld computing device, a mobile cellular phone (for example, a "smartphone"), or any other Wi-Fi-enabled device, wireless access protocol (WAP)-enabled device, or other computing device capable of interfacing directly or indirectly to the Internet or other network. The terms "user system" and "computing device" are used interchangeably herein with one another and with the term "computer." As described above, each user system 12 typically executes an HTTP client, for example, a web browsing (or simply "browsing") program, such as a web browser based on the WebKit platform, Microsoft's Internet Explorer browser, Netscape's Navigator browser, Opera's browser, Mozilla's Firefox browser, or a WAP-enabled browser in the case of a cellular phone, PDA or other wireless device, or the like, allowing a user (for example, a subscriber of on-demand services provided by the system 16) of the user system 12 to access, process and view information, pages and applications available to it from the system 16 over the network 14.

Each user system 12 also typically includes one or more user input devices, such as a keyboard, a mouse, a trackball, a touch pad, a touch screen, a pen or stylus or the like, for interacting with a graphical user interface (GUI) provided by the browser on a display (for example, a monitor screen, liquid crystal display (LCD), light-emitting diode (LED) display, among other possibilities) of the user system 12 in conjunction with pages, forms, applications and other information provided by the system 16 or other systems or servers. For example, the user interface device can be used to access data and applications hosted by system 16, and to perform searches on stored data, and otherwise allow a user to interact with various GUI pages that may be presented to a user. As discussed above, implementations are suitable for use with the Internet, although other networks can be used instead of or in addition to the Internet, such as an intranet, an extranet, a virtual private network (VPN), a non-TCP/IP based network, any LAN or WAN or the like.

The users of user systems 12 may differ in their respective capacities, and the capacity of a particular user system 12 can be entirely determined by permissions (permission levels) for the current user of such user system. For example, where a salesperson is using a particular user system 12 to interact with the system 16, that user system can have the capacities allotted to the salesperson. However, while an administrator is using that user system 12 to interact with the system 16, that user system can have the capacities allotted to that administrator. Where a hierarchical role model is used, users at one permission level can have access to applications, data, and database information accessible by a lower permission level user, but may not have access to certain applications, database information, and data accessible by a user at a higher permission level. Thus, different users generally will have different capabilities with regard to accessing and modifying application and database information, depending on the users' respective security or permission levels (also referred to as "permission sets" or "authorizations").

According to some implementations, each user system 12 and some or all of its components are operator-configurable using applications, such as a browser, including computer code executed using a central processing unit (CPU) such as an Intel Pentium® processor or the like. Similarly, the system 16 (and additional instances of an MTS, where more than one is present) and all of its components can be operator-configurable using application(s) including computer code to run using the processor system 17, which may be implemented to include a CPU, which may include an Intel Pentium® processor or the like, or multiple CPUs.

The system 16 includes tangible computer-readable media having non-transitory instructions stored thereon/in that are executable by or used to program a server or other computing system (or collection of such servers or computing systems) to perform some of the implementation of processes described herein. For example, computer program code 26 can implement instructions for operating and configuring the system 16 to intercommunicate and to process web pages, applications and other data and media content as described herein. In some implementations, the computer code 26 can be downloadable and stored on a hard disk, but the entire program code, or portions thereof, also can be stored in any other volatile or non-volatile memory medium or device as is well known, such as a ROM or RAM, or provided on any media capable of storing program code, such as any type of rotating media including floppy disks, optical discs, digital versatile disks (DVD), compact disks (CD), microdrives, and magneto-optical disks, and magnetic or optical cards, nanosystems (including molecular memory ICs), or any other type of computer-readable medium or device suitable for storing instructions or data. Additionally, the entire program code, or portions thereof, may be transmitted and downloaded from a software source over a transmission medium, for example, over the Internet, or from another server, as is well known, or transmitted over any other existing network connection as is well known (for example, extranet, VPN, LAN, etc.) using any communication medium and protocols (for example, TCP/IP, HTTP, HTTPS, Ethernet, etc.) as are well known. It will also be appreciated that computer code for the disclosed implementations can be realized in any programming language that can be executed on a server or other computing system such as, for example, C, C++, HTML, any other markup language, Java™, JavaScript, ActiveX, any other scripting language, such as VBScript, and many other programming languages as are well known may be used. (Java™ is a trademark of Sun Microsystems, Inc.).

Figure 1B:
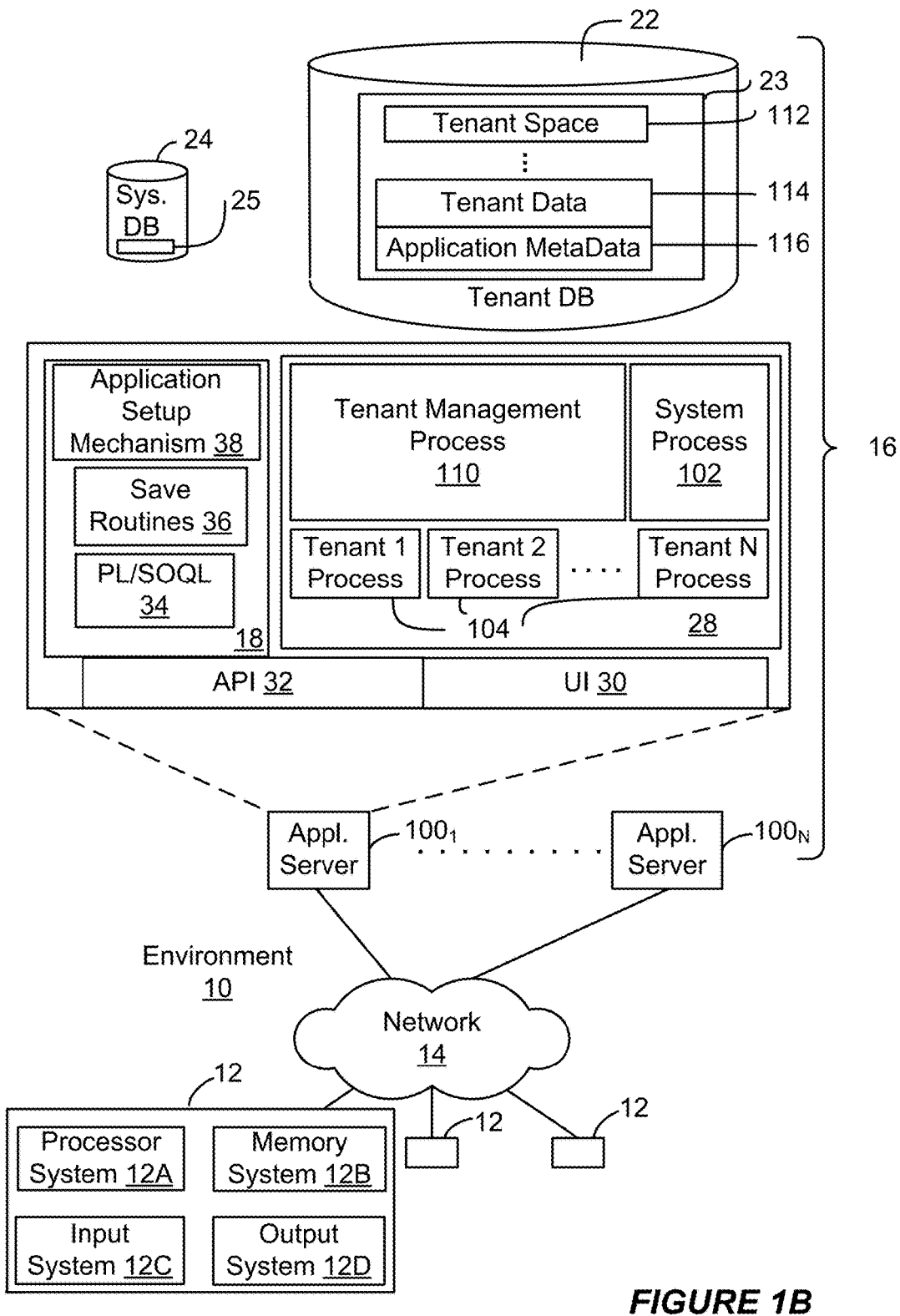
FIG. 1B shows a block diagram of example implementations of elements of FIG. 1A and example interconnections between these elements according to some implementations.

FIG. 1B shows a block diagram of example implementations of elements of FIG. 1A and example interconnections between these elements according to some implementations. That is, FIG. 1B also illustrates environment 10, but FIG. 1B, various elements of the system 16 and various interconnections between such elements are shown with more specificity according to some more specific implementations. Additionally, in FIG. 1B, the user system 12 includes a processor system 12A, a memory system 12B, an input system 12C, and an output system 12D. The processor system 12A can include any suitable combination of one or more processors. The memory system 12B can include any suitable combination of one or more memory devices. The input system 12C can include any suitable combination of input devices, such as one or more touchscreen interfaces, keyboards, mice, trackballs, scanners, cameras, or interfaces to networks. The output system 12D can include any suitable combination of output devices, such as one or more display devices, printers, or interfaces to networks.

In FIG. 1B, the network interface 20 is implemented as a set of HTTP application (or "app") servers $100_1$-$100_N$. Each of the application servers $100_1$-$100_N$ (also referred to collectively herein as "the application server 100") is configured to communicate with tenant database 22 and the tenant data 23 therein, as well as system database 24 and the system data 25 therein, to serve requests received from the user systems 12. The tenant data 23 can be divided into individual tenant storage spaces 112, which can be physically or logically arranged or divided. Within each tenant storage space 112, user storage 114 and application metadata 116 can similarly be allocated for each user. For example, a copy of a user's most recently used (MRU) items can be stored to user storage 114. Similarly, a copy of MRU items for an entire organization that is a tenant can be stored to tenant storage space 112.

The process space 28 includes system process space 102, individual tenant process spaces 104 and a tenant management process space 110. The application platform 18 includes an application setup mechanism 38 that supports application developers' creation and management of applications. Such applications and others can be saved as metadata into tenant database 22 by save routines 36 for execution by subscribers as one or more tenant process spaces 104 managed by tenant management process 110, for example. Invocations to such applications can be coded using PL/SOQL 34, which provides a programming language style interface extension to API 32. A detailed description of some PL/SOQL language implementations is discussed in commonly assigned U.S. Pat. No. 7,730,478, titled METHOD AND SYSTEM FOR ALLOWING ACCESS TO DEVELOPED APPLICATIONS VIA A MULTI-TENANT ON-DEMAND DATABASE SERVICE, by Craig Weissman, issued on Jun. 1, 2010, and hereby incorporated by reference in its entirety and for all purposes. Invocations to applications can be detected by one or more system processes, which manage retrieving application metadata 116 for the subscriber making the invocation and executing the metadata as an application in a virtual machine.

The system 16 of FIG. 1B also includes a user interface (UI) 30 and an application programming interface (API) 32 to system 16 resident processes to users or developers at user systems 12. In some other implementations, the environment 10 may not have the same elements as those listed above or may have other elements instead of, or in addition to, those listed above.

Each application server 100 can be communicably coupled with tenant database 22 and system database 24, for example, having access to tenant data 23 and system data 25, respectively, via a different network connection. For example, one application server $100_1$ can be coupled via the network 14 (for example, the Internet), another application server $100_{N-1}$ can be coupled via a direct network link, and another application server $100_N$ can be coupled by yet a different network connection. Transfer Control Protocol and Internet Protocol (TCP/IP) are examples of typical protocols that can be used for communicating between application servers 100 and the system 16. However, it will be apparent to one skilled in the art that other transport protocols can be used to optimize the system 16 depending on the network interconnections used.

In some implementations, each application server 100 is configured to handle requests for any user associated with any organization that is a tenant of the system 16. Because it can be desirable to be able to add and remove application servers 100 from the server pool at any time and for various reasons, in some implementations there is no server affinity for a user or organization to a specific application server 100. In some such implementations, an interface system implementing a load balancing function (for example, an F5 Big-IP load balancer) is communicably coupled between the application servers 100 and the user systems 12 to distribute requests to the application servers 100. In one implementation, the load balancer uses a least-connections algorithm to route user requests to the application servers 100. Other examples of load balancing algorithms, such as round robin and observed-response-time, also can be used. For example, in some instances, three consecutive requests from the same user could hit three different application servers 100, and three requests from different users could hit the same application server 100. In this manner, by way of example, system 16 can be a multi-tenant system in which system 16 handles storage of, and access to, different objects, data and applications across disparate users and organizations.

In one example storage use case, one tenant can be a company that employs a sales force where each salesperson uses system 16 to manage aspects of their sales. A user can maintain contact data, leads data, customer follow-up data, performance data, goals and progress data, etc., all applicable to that user's personal sales process (for example, in tenant database 22). In an example of a MTS arrangement, because all of the data and the applications to access, view, modify, report, transmit, calculate, etc., can be maintained and accessed by a user system 12 having little more than network access, the user can manage his or her sales efforts and cycles from any of many different user systems. For example, when a salesperson is visiting a customer and the customer has Internet access in their lobby, the salesperson can obtain critical updates regarding that customer while waiting for the customer to arrive in the lobby.

While each user's data can be stored separately from other users' data regardless of the employers of each user, some data can be organization-wide data shared or accessible by several users or all of the users for a given organization that is a tenant. Thus, there can be some data structures managed by system 16 that are allocated at the tenant level while other data structures can be managed at the user level. Because an MTS can support multiple tenants including possible competitors, the MTS can have security protocols that keep data, applications, and application use separate. Also, because many tenants may opt for access to an MTS rather than maintain their own system, redundancy, up-time, and backup are additional functions that can be implemented in the MTS. In addition to user-specific data and tenant-specific data, the system 16 also can maintain system level data usable by multiple tenants or other data. Such system level data can include industry reports, news, postings, and the like that are sharable among tenants.

In some implementations, the user systems 12 (which also can be client systems) communicate with the application servers 100 to request and update system-level and tenant-level data from the system 16. Such requests and updates can involve sending one or more queries to tenant database 22 or system database 24. The system 16 (for example, an application server 100 in the system 16) can automatically generate one or more SQL statements (for example, one or more SQL queries) designed to access the desired information. System database 24 can generate query plans to access the requested data from the database. The term "query plan" generally refers to one or more operations used to access information in a database system.

Each database can generally be viewed as a collection of objects, such as a set of logical tables, containing data fitted into predefined or customizable categories. A "table" is one representation of a data object, and may be used herein to simplify the conceptual description of objects and custom objects according to some implementations. It should be understood that "table" and "object" may be used interchangeably herein. Each table generally contains one or more data categories logically arranged as columns or fields in a viewable schema. Each row or element of a table can contain an instance of data for each category defined by the fields. For example, a CRM database can include a table that describes a customer with fields for basic contact information such as name, address, phone number, fax number, etc. Another table can describe a purchase order, including fields for information such as customer, product, sale price, date, etc. In some MTS implementations, standard entity tables can be provided for use by all tenants. For CRM database applications, such standard entities can include tables for case, account, contact, lead, and opportunity data objects, each containing pre-defined fields. As used herein, the term "entity" also may be used interchangeably with "object" and "table."

In some MTS implementations, tenants are allowed to create and store custom objects, or may be allowed to customize standard entities or objects, for example by creating custom fields for standard objects, including custom index fields. Commonly assigned U.S. Pat. No. 7,779,039, titled CUSTOM ENTITIES AND FIELDS IN A MULTI-TENANT DATABASE SYSTEM, by Weissman et al., issued on Aug. 17, 2010, and hereby incorporated by reference in its entirety and for all purposes, teaches systems and methods for creating custom objects as well as customizing standard objects in a multi-tenant database system. In some implementations, for example, all custom entity data rows are stored in a single multi-tenant physical table, which may contain multiple logical tables per organization. It is transparent to customers that their multiple "tables" are in fact stored in one large table or that their data may be stored in the same table as the data of other customers.

Figure 2A:
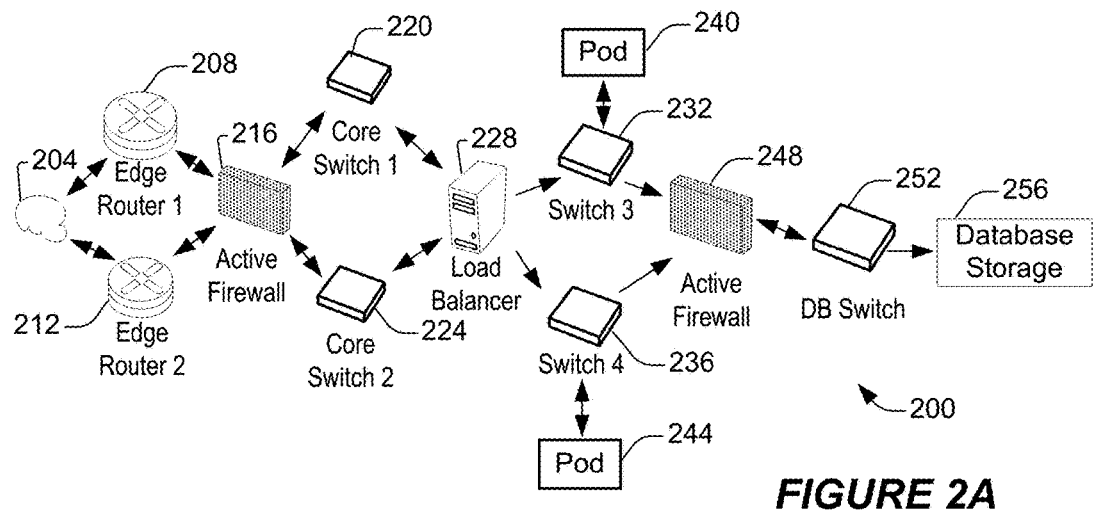
FIG. 2A shows a system diagram of example architectural components of an on-demand database service environment according to some implementations.

FIG. 2A shows a system diagram illustrating example architectural components of an on-demand database service environment 200 according to some implementations. A client machine communicably connected with the cloud 204, generally referring to one or more networks in combination, as described herein, can communicate with the on-demand database service environment 200 via one or more edge routers 208 and 212. A client machine can be any of the examples of user systems 12 described above. The edge routers can communicate with one or more core switches 220 and 224 through a firewall 216. The core switches can communicate with a load balancer 228, which can distribute server load over different pods, such as the pods 240 and 244. The pods 240 and 244, which can each include one or more servers or other computing resources, can perform data processing and other operations used to provide on-demand services. Communication with the pods can be conducted via pod switches 232 and 236. Components of the on-demand database service environment can communicate with database storage 256 through a database firewall 248 and a database switch 252.

Figure 2B:
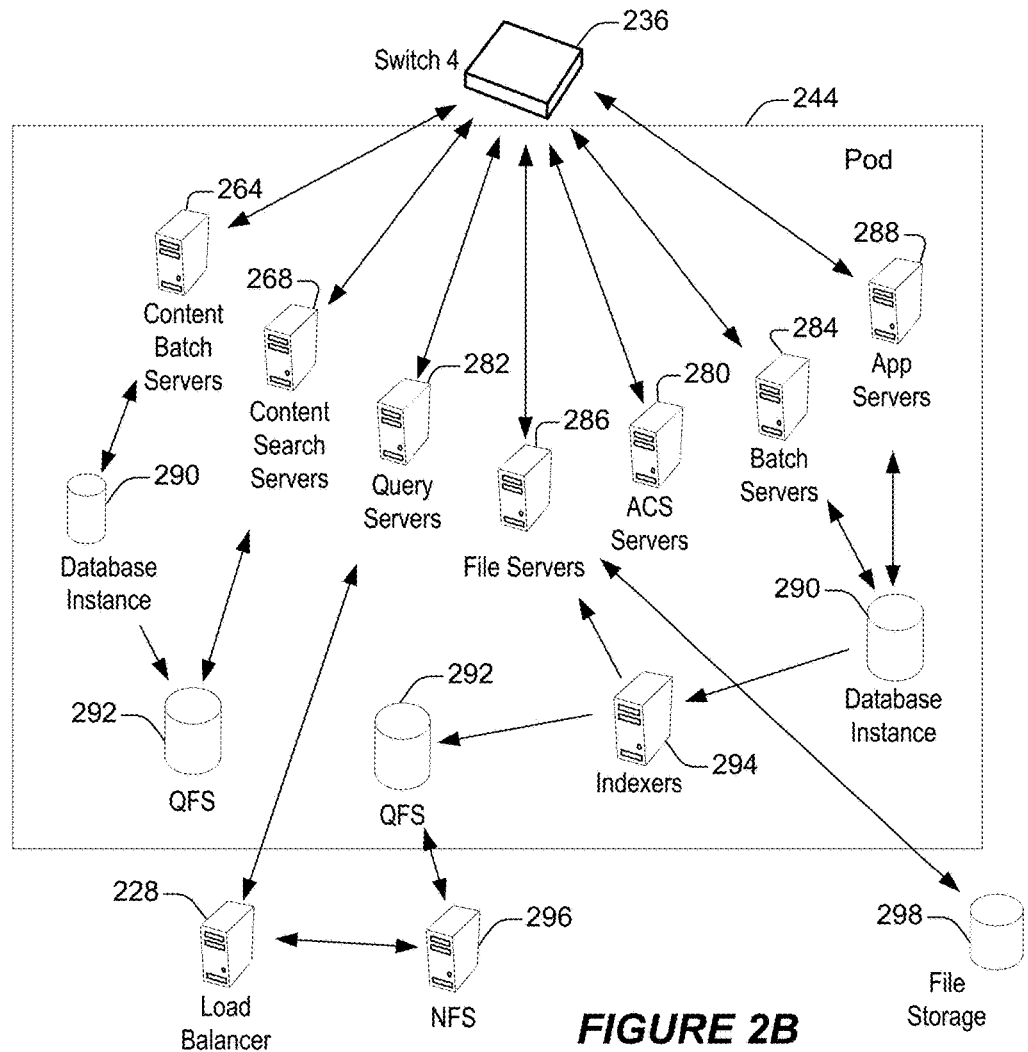
FIG. 2B shows a system diagram further illustrating example architectural components of an on-demand database service environment according to some implementations.

As shown in FIGS. 2A and 2B, accessing an on-demand database service environment can involve communications transmitted among a variety of different hardware or software components. Further, the on-demand database service environment 200 is a simplified representation of an actual on-demand database service environment. For example, while only one or two devices of each type are shown in FIGS. 2A and 2B, some implementations of an on-demand database service environment can include anywhere from one to several devices of each type. Also, the on-demand database service environment need not include each device shown in FIGS. 2A and 2B, or can include additional devices not shown in FIGS. 2A and 2B.

Additionally, it should be appreciated that one or more of the devices in the on-demand database service environment 200 can be implemented on the same physical device or on different hardware. Some devices can be implemented using hardware or a combination of hardware and software. Thus, terms such as "data processing apparatus," "machine," "server" and "device" as used herein are not limited to a single hardware device, rather references to these terms can include any suitable combination of hardware and software configured to provide the described functionality.

The cloud 204 is intended to refer to a data network or multiple data networks, often including the Internet. Client machines communicably connected with the cloud 204 can communicate with other components of the on-demand database service environment 200 to access services provided by the on-demand database service environment. For example, client machines can access the on-demand database service environment to retrieve, store, edit, or process information. In some implementations, the edge routers 208 and 212 route packets between the cloud 204 and other components of the on-demand database service environment 200. For example, the edge routers 208 and 212 can employ the Border Gateway Protocol (BGP). The BGP is the core routing protocol of the Internet. The edge routers 208 and 212 can maintain a table of IP networks or 'prefixes', which designate network reachability among autonomous systems on the Internet.

In some implementations, the firewall 216 can protect the inner components of the on-demand database service environment 200 from Internet traffic. The firewall 216 can block, permit, or deny access to the inner components of the on-demand database service environment 200 based upon a set of rules and other criteria. The firewall 216 can act as one or more of a packet filter, an application gateway, a stateful filter, a proxy server, or any other type of firewall.

In some implementations, the core switches 220 and 224 are high-capacity switches that transfer packets within the on-demand database service environment 200. The core switches 220 and 224 can be configured as network bridges that quickly route data between different components within the on-demand database service environment. In some implementations, the use of two or more core switches 220 and 224 can provide redundancy or reduced latency.

In some implementations, the pods 240 and 244 perform the core data processing and service functions provided by the on-demand database service environment. Each pod can include various types of hardware or software computing resources. An example of the pod architecture is discussed in greater detail with reference to FIG. 2B. In some implementations, communication between the pods 240 and 244 is conducted via the pod switches 232 and 236. The pod switches 232 and 236 can facilitate communication between the pods 240 and 244 and client machines communicably connected with the cloud 204, for example via core switches 220 and 224. Also, the pod switches 232 and 236 may facilitate communication between the pods 240 and 244 and the database storage 256. In some implementations, the load balancer 228 can distribute workload between the pods 240 and 244. Balancing the on-demand service requests between the pods can assist in improving the use of resources, increasing throughput, reducing response times, or reducing overhead. The load balancer 228 may include multilayer switches to analyze and forward traffic.

In some implementations, access to the database storage 256 is guarded by a database firewall 248. The database firewall 248 can act as a computer application firewall operating at the database application layer of a protocol stack. The database firewall 248 can protect the database storage 256 from application attacks such as structure query language (SQL) injection, database rootkits, and unauthorized information disclosure. In some implementations, the database firewall 248 includes a host using one or more forms of reverse proxy services to proxy traffic before passing it to a gateway router. The database firewall 248 can inspect the contents of database traffic and block certain content or database requests. The database firewall 248 can work on the SQL application level atop the TCP/IP stack, managing applications' connection to the database or SQL management interfaces as well as intercepting and enforcing packets traveling to or from a database network or application interface.

In some implementations, communication with the database storage 256 is conducted via the database switch 252. The multi-tenant database storage 256 can include more than one hardware or software components for handling database queries. Accordingly, the database switch 252 can direct database queries transmitted by other components of the on-demand database service environment (for example, the pods 240 and 244) to the correct components within the database storage 256. In some implementations, the database storage 256 is an on-demand database system shared by many different organizations as described above with reference to FIGS. 1A and 1B.

FIG. 2B shows a system diagram further illustrating example architectural components of an on-demand database service environment according to some implementations. The pod 244 can be used to render services to a user of the on-demand database service environment 200. In some implementations, each pod includes a variety of servers or other systems. The pod 244 includes one or more content batch servers 264, content search servers 268, query servers 282, file force servers 286, access control system (ACS) servers 280, batch servers 284, and app servers 288. The pod 244 also can include database instances 290, quick file systems (QFS) 292, and indexers 294. In some implementations, some or all communication between the servers in the pod 244 can be transmitted via the switch 236.

In some implementations, the app servers 288 include a hardware or software framework dedicated to the execution of procedures (for example, programs, routines, scripts) for supporting the construction of applications provided by the on-demand database service environment 200 via the pod 244. In some implementations, the hardware or software framework of an app server 288 is configured to execute operations of the services described herein, including performance of the blocks of various methods or processes described herein. In some alternative implementations, two or more app servers 288 can be included and cooperate to perform such methods, or one or more other servers described herein can be configured to perform the disclosed methods.

The content batch servers 264 can handle requests internal to the pod. Some such requests can be long-running or not tied to a particular customer. For example, the content batch servers 264 can handle requests related to log mining, cleanup work, and maintenance tasks. The content search servers 268 can provide query and indexer functions. For example, the functions provided by the content search servers 268 can allow users to search through content stored in the on-demand database service environment. The file force servers 286 can manage requests for information stored in the Fileforce storage 298. The Fileforce storage 298 can store information such as documents, images, and basic large objects (BLOBs). By managing requests for information using the file force servers 286, the image footprint on the database can be reduced. The query servers 282 can be used to retrieve information from one or more file systems. For example, the query system 282 can receive requests for information from the app servers 288 and transmit information queries to the NFS 296 located outside the pod.

The pod 244 can share a database instance 290 configured as a multi-tenant environment in which different organizations share access to the same database. Additionally, services rendered by the pod 244 may call upon various hardware or software resources. In some implementations, the ACS servers 280 control access to data, hardware resources, or software resources. In some implementations, the batch servers 284 process batch jobs, which are used to run tasks at specified times. For example, the batch servers 284 can transmit instructions to other servers, such as the app servers 288, to trigger the batch jobs.

In some implementations, the QFS 292 is an open source file system available from Sun Microsystems® of Santa Clara, Calif. The QFS can serve as a rapid-access file system for storing and accessing information available within the pod 244. The QFS 292 can support some volume management capabilities, allowing many disks to be grouped together into a file system. File system metadata can be kept on a separate set of disks, which can be useful for streaming applications where long disk seeks cannot be tolerated. Thus, the QFS system can communicate with one or more content search servers 268 or indexers 294 to identify, retrieve, move, or update data stored in the network file systems 296 or other storage systems.

In some implementations, one or more query servers 282 communicate with the NFS 296 to retrieve or update information stored outside of the pod 244. The NFS 296 can allow servers located in the pod 244 to access information to access files over a network in a manner similar to how local storage is accessed. In some implementations, queries from the query servers 282 are transmitted to the NFS 296 via the load balancer 228, which can distribute resource requests over various resources available in the on-demand database service environment. The NFS 296 also can communicate with the QFS 292 to update the information stored on the NFS 296 or to provide information to the QFS 292 for use by servers located within the pod 244.

In some implementations, the pod includes one or more database instances 290. The database instance 290 can transmit information to the QFS 292. When information is transmitted to the QFS, it can be available for use by servers within the pod 244 without using an additional database call. In some implementations, database information is transmitted to the indexer 294. Indexer 294 can provide an index of information available in the database 290 or QFS 292. The index information can be provided to file force servers 286 or the QFS 292.

II. Enterprise Social Networking

As described above, in some implementations the database system 16 includes application servers $100_1$-$100_N$ that can implement or host one or more applications or platforms for providing various on-demand or cloud-computing features or services described herein. In some implementations, one or more of the application servers $100_1$-$100_N$ implement or host an enterprise social networking platform. In some implementations, the enterprise social networking platform enables each tenant of the database system 16 to create, customize, build or access an enterprise social network for use by users of the respective organization (tenant).

Enterprise social networks can be implemented in various settings, including businesses, organizations and other enterprises (all of which are used interchangeably herein). For instance, an enterprise social network can be implemented to connect users within a business corporation, partnership or organization, or a group of users within such an enterprise. For instance, Chatter® can be used by users who are employees in a business organization to share data, communicate, and collaborate with each other for various enterprise-related purposes. Some of the disclosed methods, processes, devices, systems and computer-readable storage media described herein can be configured or designed for use in a multi-tenant database environment, such as described above with respect to database system 16. In an example implementation, each organization or a group within the organization can be a respective tenant of the system.

In some implementations, each user of the database system 16 is associated with a "user profile." A user profile refers generally to a collection of data about a given user. The data can include general information, such as a name, a title, a phone number, a photo, a biographical summary, or a status (for example, text describing what the user is currently doing, thinking or expressing). The data associated with a user profile also can include various permissions defining the ability of the user to interact with various data objects. In implementations in which there are multiple tenants, a user is typically associated with a particular tenant (or "organization"). For example, a user could be a salesperson of an organization that is a tenant of the database system 16.

A "group" generally refers to a collection of users within an organization. In some implementations, a group can be defined as users with the same or a similar attribute, or by membership or subscription. Groups can have various visibilities to users within an enterprise social network. For example, some groups can be private while others can be public. In some implementations, to become a member within a private group, and to have the capability to publish and view feed items on the group's group feed, a user must request to be subscribed to the group (and be accepted by, for example, an administrator or owner of the group), be invited to subscribe to the group (and accept), or be directly subscribed to the group (for example, by an administrator or owner of the group). In some implementations, any user within the enterprise social network can subscribe to or follow a public group (and thus become a "member" of the public group) within the enterprise social network.

In some implementations, a "community" refers to a collection of one or more users within an organization that is a tenant of the database system 16 and one or more persons or enterprises outside of the organization that may or may not necessarily be tenants of the database system 16. For example, a community can enable users of an organization to connect with various partners outside of the organization including various third-party partners outside of the social networking system to facilitate one or more shared goals, objectives, or activities. For example, such partners can include distributors, resellers and suppliers, among other desirable partners. In some implementations, multiple communities can be created for or by an organization for different purposes and for connecting or collaborating with different partners. In some implementations, a community also can have a community feed.

A "record" generally refers to a data entity, such as an instance of a data object created by a user or a group of users of the database system 16. Such records can include, for example, data objects representing and maintaining data for accounts (for example, representing a business relationship with another enterprise). In some implementations, each record is assigned a record type, which can be identified by a RecordTypeID. Examples of account record types include: customers (for example, users or organizations who pay the enterprise money), customer support (for example, users or organizations who pay the enterprise money to support them), households (for example, organizations in a business-to-consumer model), partners (for example, organizations who pay the enterprise money and to whom the enterprise pays money), suppliers (for example, organizations to whom the enterprise pays money), and other organizations including organizations with whom no money is exchanged. Other examples of record types in addition to accounts can include cases, opportunities, leads, projects, contracts, orders, pricebooks, products, solutions, reports and forecasts, among other possibilities.

For example, an account record can be for a business partner or potential business partner, an actual or potential customer, an actual or potential supplier, an actual or potential distributor, or a client, among other possibilities. A record such as an account can include information describing an entire enterprise or subsidiary of an enterprise. As another example, a record such as an account record itself can include a number of records. For example, a customer account can include opportunities, contracts, and orders. As another example, a partner record can include a project or contract that a user or group of users is working on with an existing partner, or a project or contract that the user is trying to obtain with a partner. A record also can include various data fields and controls that are defined by the structure or layout of the object (for example, fields of certain data types and purposes). A record also can have custom fields defined by a user or organization. A field can include (or include a link to) another record, thereby providing a parent-child relationship between the records.

Records also can have various visibilities to users within an enterprise social network. For example, some records can be private while others can be public. In some implementations, to access a private record, and to have the capability to publish and view feed items on the record's record feed, a user must request to be subscribed to the record (and be accepted by, for example, an administrator or owner of the record), be invited to subscribe to the record (and accept), be directly subscribed to the record or be shared the record (for example, by an administrator or owner of the record). In some implementations, any user within the enterprise social network can subscribe to or follow a public record within the enterprise social network.

In some online enterprise social networks, users also can follow one another by establishing "links" or "connections" with each other, sometimes referred to as "friending" one another. By establishing such a link, one user can see information generated by, generated about, or otherwise associated with another user. For instance, a first user can see information posted by a second user to the second user's profile page. In one example, when the first user is following the second user, the first user's news feed can receive a post from the second user submitted to the second user's profile feed.

In some implementations, users can access one or more enterprise network feeds (also referred to herein simply as "feeds"), which include publications presented as feed items or entries in the feed. A network feed can be displayed in a graphical user interface (GUI) on a display device such as the display of a user's computing device as described above. The publications can include various enterprise social network information or data from various sources and can be stored in the database system 16, for example, in tenant database 22. In some implementations, feed items of information for or about a user can be presented in a respective user feed, feed items of information for or about a group can be presented in a respective group feed, and feed items of information for or about a record can be presented in a respective record feed. A second user following a first user, a first group, or a first record can automatically receive the feed items associated with the first user, the first group or the first record for display in the second user's news feed. In some implementations, a user feed also can display feed items from the group feeds of the groups the respective user subscribes to, as well as feed items from the record feeds of the records the respective user subscribes to.

The term "feed item" (or feed element) refers to an item of information, which can be viewable in a feed. Feed items can include publications such as messages (for example, user-generated textual posts or comments), files (for example, documents, audio data, image data, video data or other data), and "feed-tracked" updates associated with a user, a group or a record (feed-tracked updates are described in greater detail below). A feed item, and a feed in general, can include combinations of messages, files and feed-tracked updates. Documents and other files can be included in, linked with, or attached to a post or comment. For example, a post can include textual statements in combination with a document. The feed items can be organized in chronological order or another suitable or desirable order (which can be customizable by a user) when the associated feed is displayed in a graphical user interface (GUI), for instance, on the user's computing device.

Messages such as posts can include alpha-numeric or other character-based user inputs such as words, phrases, statements, questions, emotional expressions, or symbols. In some implementations, a comment can be made on any feed item. In some implementations, comments are organized as a list explicitly tied to a particular feed item such as a feed-tracked update, post, or status update. In some implementations, comments may not be listed in the first layer (in a hierarchal sense) of feed items, but listed as a second layer branching from a particular first layer feed item (such as a feed-tracked update, post, or status update). In some implementations, a "like" or "dislike" also can be submitted in response to a particular post, comment or other publication.

A "feed-tracked update," also referred to herein as a "feed update," is another type of publication that may be presented as a feed item and generally refers to data representing an event. A feed-tracked update can include text generated by the database system in response to the event, to be provided as one or more feed items for possible inclusion in one or more feeds. In one implementation, the data can initially be stored by the database system in, for example, tenant database 22, and subsequently used by the database system to create text for describing the event. Both the data and the text can be a feed-tracked update, as used herein. In some implementations, an event can be an update of a record and can be triggered by a specific action by a user. Which actions trigger an event can be configurable. Which events have feed-tracked updates created and which feed updates are sent to which users also can be configurable. Messages and feed updates can be stored as a field or child object of a record. For example, the feed can be stored as a child object of the record.

As described above, a network feed can be specific to an individual user of an online social network. For instance, a user news feed (or "user feed") generally refers to an aggregation of feed items generated for a particular user, and in some implementations, is viewable only to the respective user on a home page of the user. In some implementations a user profile feed (also referred to as a "user feed") is another type of user feed that refers to an aggregation of feed items generated by or for a particular user, and in some implementations, is viewable only by the respective user and other users following the user on a profile page of the user. As a more specific example, the feed items in a user profile feed can include posts and comments that other users make about or send to the particular user, and status updates made by the particular user. As another example, the feed items in a user profile feed can include posts made by the particular user and feed-tracked updates initiated based on actions of the particular user.

As is also described above, a network feed can be specific to a group of enterprise users of an online enterprise social network. For instance, a group news feed (or "group feed") generally refers to an aggregation of feed items generated for or about a particular group of users of the database system 16 and can be viewable by users following or subscribed to the group on a profile page of the group. For example, such feed items can include posts made by members of the group or feed-tracked updates about changes to the respective group (or changes to documents or other files shared with the group). Members of the group can view and post to a group feed in accordance with a permissions configuration for the feed and the group. Publications in a group context can include documents, posts, or comments. In some implementations, the group feed also includes publications and other feed items that are about the group as a whole, the group's purpose, the group's description, a status of the group, and group records and other objects stored in association with the group. Threads of publications including updates and messages, such as posts, comments, likes, etc., can define conversations and change over time. The following of a group allows a user to collaborate with other users in the group, for example, on a record or on documents or other files (which may be associated with a record).

As is also described above, a network feed can be specific to a record in an online enterprise social network. For instance, a record news feed (or "record feed") generally refers to an aggregation of feed items about a particular record in the database system 16 and can be viewable by users subscribed to the record on a profile page of the record. For example, such feed items can include posts made by users about the record or feed-tracked updates about changes to the respective record (or changes to documents or other files associated with the record). Subscribers to the record can view and post to a record feed in accordance with a permissions configuration for the feed and the record. Publications in a record context also can include documents, posts, or comments. In some implementations, the record feed also includes publications and other feed items that are about the record as a whole, the record's purpose, the record's description, and other records or other objects stored in association with the record. Threads of publications including updates and messages, such as posts, comments, likes, etc., can define conversations and change over time. The following of a record allows a user to track the progress of that record and collaborate with other users subscribing to the record, for example, on the record or on documents or other files associated with the record.

Figure 3:
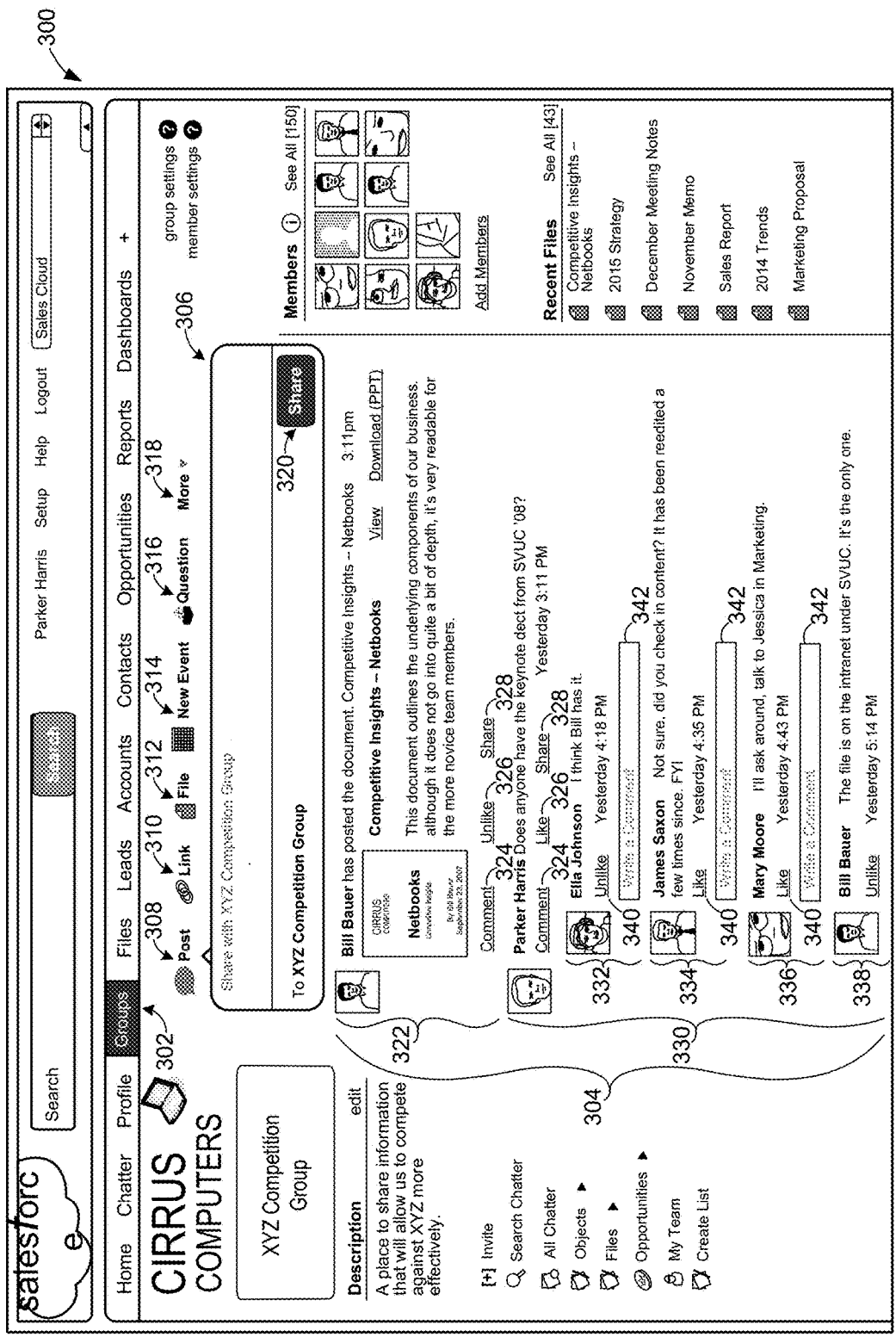
FIG. 3 shows an example of a web interface for a group page including a group feed for interacting with members of the group in an enterprise social network according to some implementations.

FIG. 3 shows an example of a web interface 300 for a group page including a group feed for interacting with members of the group in an enterprise social network according to some implementations. For example, the database system 16 can generate the interface 300 and transmit it to a user's computer (for example, as an HTML structured document) over one or more networks for rendering by a web browser or other rendering engine executing within the user's computer. The interface 300 can include multiple primary tabs for accessing various information or data. The primary tabs include a Groups tab 302 that, when "clicked" or otherwise selected by a user (as is the case in FIG. 3), opens a page displaying various information or UI elements for a group (or groups) in a section or area below the primary tabs.

The primary tabs of the interface 300 can be customizable by a user or by an administrator for the user's organization. For example, the primary tabs of the interface also can include a Home tab that opens the user's home page, a Chatter® tab that displays Chatter®-related information includes a personal news feed, a Profile tab that opens the user's profile page, a Files tab that opens a page displaying various information or UI elements associated with the file records the user owns or is subscribed to. Other primary tabs can include a Leads tab, an Accounts tab, an Opportunities tab, a Reports tab, a Dashboard tab, and a Contacts tab (in some implementations, the contacts are third-party contacts that are not registered users of the enterprise social network). Depending on which of the primary tabs described above is selected, the interface 300 can include one or more sub-tabs, buttons, links or other UI elements that can be selected to facilitate collaboration or the completion of a workflow.

As just described, the Groups tab 302 is selected in FIG. 3. In the illustrated example, the interface 300 displays a group page for the group "XYZ Competitive Group." The interface 300 includes a group feed 304 for the group in a section below the primary tabs. The interface 300 includes a publication window 306 at a top portion of the group feed 304 that enables the user to submit a publication to the group feed. In the illustrated example implementation, the user can select a format or context for the publication by selecting the "Post" sub-tab 308, the "Link" sub-tab 310, the "File" sub-tab 312, a "New Event" sub-tab 314 or the "Question" sub-tab 316 or a "More" sub-tab 318. The arrangement of the publication window 306 and the number and function of various UI elements displayed in the publication window 306 can be tailored to a specific type of publication depending on which of the sub-tabs is selected to facilitate the publication. For example, the Post sub-tab 308 (selected in the illustrated example) enables the user to enter content in the form of text in the publication window 306. The user can also elect to reference other users, groups or records by, for example, @-mentioning such users, groups or records. The user can submit (publish) the publication by selecting a "Share" button 320. As another example, the Link sub-tab 310 enables the user to publish a link such as a URL or other address to the feed (note that this instance of the term "link" is not to be used interchangeably with the terms "subscription," "association," or "following" or other derivations or conjugations of these terms as described above). As another example, the File sub-tab 312 enables a user to publish a file to the feed as well as to enter text describing the file or otherwise relating to the file. As another example, the New Event sub-tab 314 enables the user to share an event invitation or to describe an event. As another example, the Question sub-tab 316 enables a user to publish a question. In some implementations, a published question can be distinguished from a normal post by the manner the question is displayed in a feed item or by the manner in which other users are notified of its publication. Furthermore, the More sub-tab 320 can allow a user to perform or cause other actions. For example, upon a user selecting the More sub-tab 320, a drop-down menu or pick list can be displayed below providing the user with selectable options or actions the user can choose.

As shown, the group feed 304 includes feed items published by other users. For example, the group feed 304 includes a first feed item 322 that includes a file and a related description published by the user "Bill Bauer." As shown, the user viewing the group feed 304 can select to comment on the publication, like the publication or share the publication via Comment, Like and Share buttons or links 324, 326, and 328, respectively. For example, when the user selects the Comment link 324, a comment window can be displayed in the feed item 322 in an area below the original publication. In some implementations, after the user viewing the group feed 304 has selected to "like" the publication via the Like link 326, the Like link can be transformed to an "Unlike" link enabling the user to unlike the publication. In some implementations, after a user selects the Share link 328, a pop-up window can be displayed enabling the user to select other users, groups or records for which to share the feed item 322. Also shown in the group feed is a second feed item 330 that includes a post published by the user "Parker Harris." As shown, other users, including Ella Johnson, James Saxon, Mary Moore and Bill Bauer have submitted comments 332, 334, 336 and 338, respectively, on the publication submitted by Parker Harris. In some implementations, the user viewing the group feed 304 can like the individual comments via Like links 340 or comment on individual comments via comment fields 342.

Figure 4:
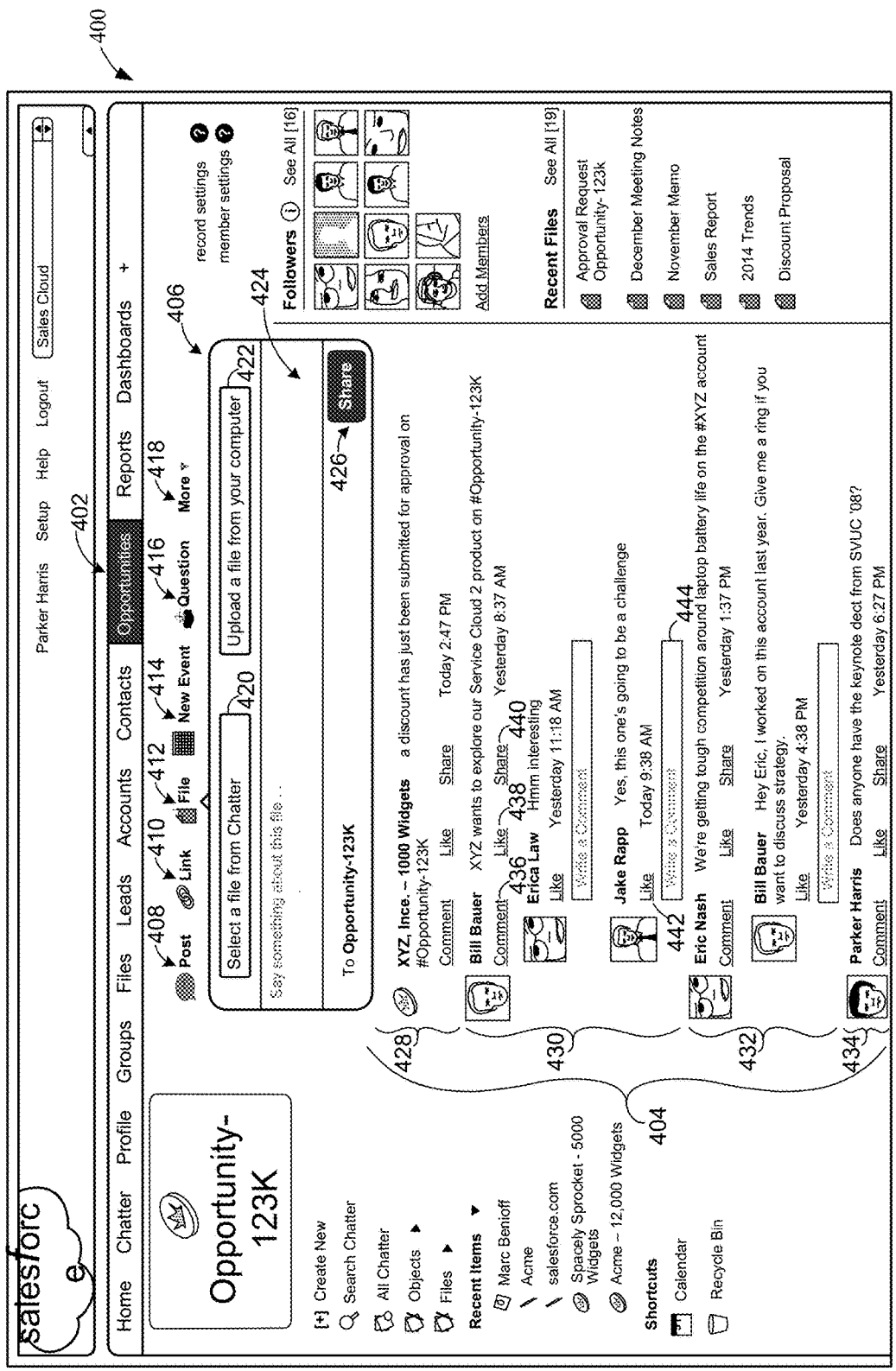
FIG. 4 shows an example of a web interface for a record page including a record feed for interacting with followers of the record in an enterprise social network according to some implementations.

FIG. 4 shows an example of a web interface 400 for a record page including a record feed for interacting with followers of the record in an enterprise social network according to some implementations. The Opportunities tab 402 is selected in FIG. 4. In the illustrated example, the interface 400 displays an opportunity page (a type of record page) for the opportunity "Opportunity-123K." The interface 400 includes a record feed 404 for the opportunity in a section below the primary tabs. The interface 400 includes a publication window 406 at a top portion of the record feed 404 that enables the user to submit a publication to the record feed. In the illustrated example implementation, the user can select a format or context for the publication by selecting a Post sub-tab 408, a Link sub-tab 410, a File sub-tab 412, a New Event sub-tab 414, a Question sub-tab 416 or a More sub-tab 418. As described above with reference to the group feed 404 of FIG. 4, the arrangement of the publication window 406 and the number and function of various UI elements displayed in the publication window 406 can be tailored to a specific type of publication depending on which of the sub-tabs is selected to facilitate the publication. In the illustrated example, the File sub-tab 412 is selected. The user can select a file to include in the publication via elements 420 or 422. The user also can add a description of the file or other information about the file in a body field 424. The user can also elect to reference other users, groups or records by, for example, @-mentioning such users, groups or records. The user can submit (publish) the publication by selecting a "Share" button 426.

As shown, the record feed 404 includes feed items published by other users. For example, the record feed 404 includes a number of feed items 428, 430, 432 and 434. Similar to the group feed 304 shown and described with reference to FIG. 3, the user viewing the record feed 404 can select to comment on the publications, like the publications or share the publications via Comment, Like and Share buttons or links 436, 438, and 440, respectively. As also described above, the user viewing the record feed 404 can like the individual comments via Like links 442 or comment on individual comments via comment fields 444.

Figure 5:
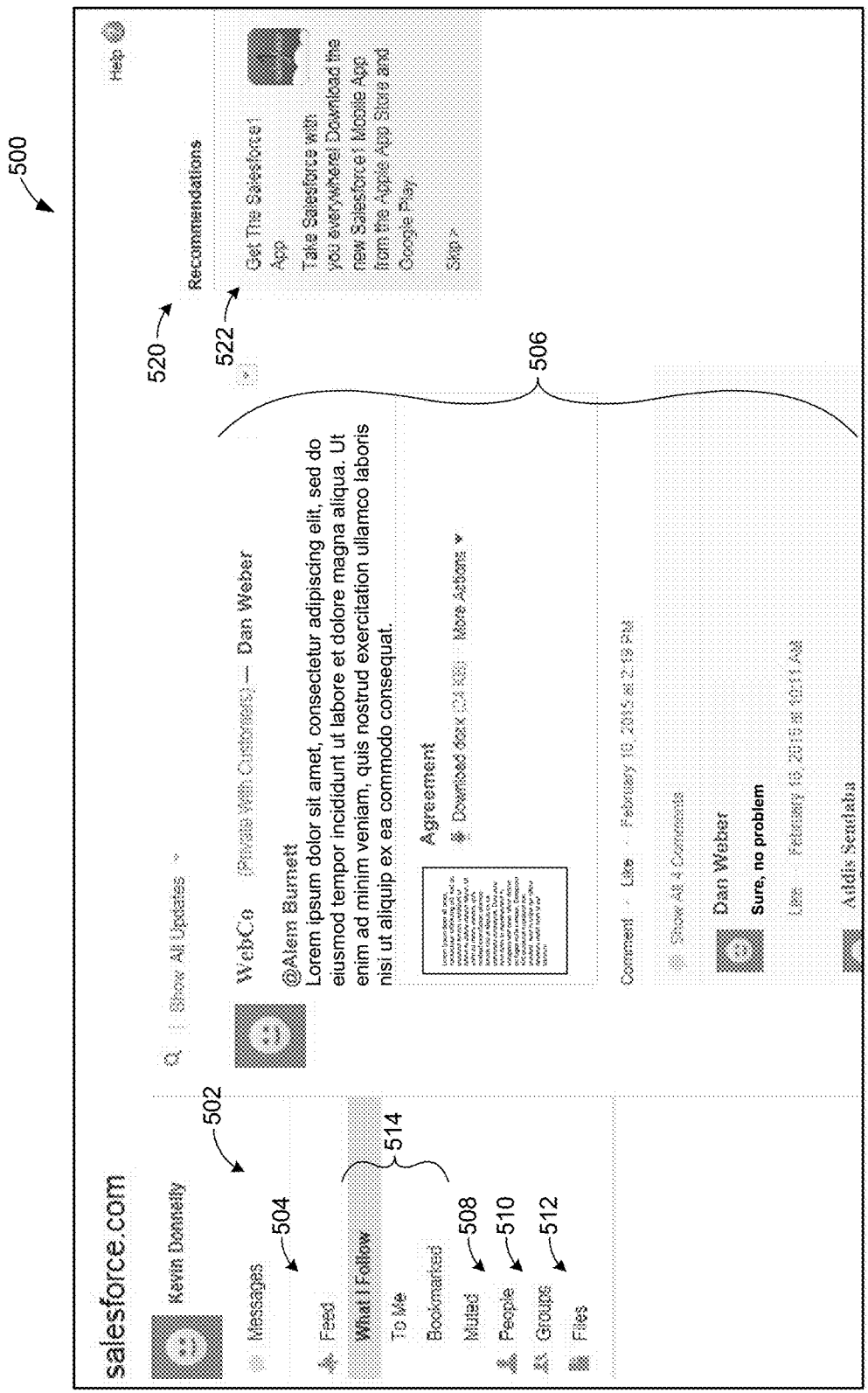
FIG. 5 shows an example of a web interface for a user page including a user feed for interacting with other users of an enterprise social network according to some implementations.

FIG. 5 shows an example of a web interface 500 for a user page including a user feed for interacting with other users of an enterprise social network according to some implementations. The interface 500 includes a section 502 in which the user can select various information to view in the interface 500. For example, the user can select a "Feed" button or tab 504 to view a user feed 506, a "People" button 508 to view other users the user follows or who follow the user, a "Groups" button 510 to view Groups the user is a member of, a "Files" button 512 to view files the user has created, edited, used or otherwise has access to. In the illustrated example, the Feed button 504 is selected resulting in the display of the user feed 506. In some implementations, when the Feed button 504 is selected, a picklist 514 of various filters can be displayed below the Feed button 504 enabling the user to filter the feed items to be displayed in the user feed 506. For example, the user can select a "What I Follow" filter (currently selected in the illustrated example) to view feed items associated with other users, groups and records the user subscribes to. The user also can select other filters such as a "To Me" filter to view feed items shared with or otherwise targeted to the user, a "Bookmarked" filter to view feed items that the user has selected to bookmark, and an "All Company" filter to view all of the feed items for the entire organization. The web interface 500 also includes a "Recommendations" section 520 that can display one or more recommendations to the user. In the illustrated example, the Recommendations section 520 displays a recommendation 520 suggestion an application that the user may be interested in learning more about or purchasing. In some implementations, the Recommendations section 520 also can display other users the user may be interested in following, groups the user may be interested in subscribing to, communities the user may be interesting in joining, other products or services the user may be interested in learning about or purchasing, as well as events (for example, conferences, classes, seminars, webinars or activities) the user may be interested in joining, attending or otherwise participating in.

III. Enterprise Social Networking Architecture

In some implementations, data is stored in database system 16, including tenant database 22, in the form of "entity objects" (also referred to herein simply as "entities"). In some implementations, entities are categorized into "Records objects" and "Collaboration objects." In some such implementations, the Records object includes all records in the enterprise social network. Each record can be considered a sub-object of the overarching Records object. In some implementations, Collaboration objects include, for example, a "Users object," a "Groups object," a "Group-User relationship object," a "Record-User relationship object" and a "Feed Items object."

In some implementations, the Users object is a data structure that can be represented or conceptualized as a "Users Table" that associates users to information about or pertaining to the respective users including, for example, metadata about the users. In some implementations, the Users Table includes all of the users within an organization. In some other implementations, there can be a Users Table for each division, department, team or other sub-organization within an organization. In implementations in which the organization is a tenant of a multi-tenant enterprise social network platform, the Users Table can include all of the users within all of the organizations that are tenants of the multi-tenant enterprise social network platform. In some implementations, each user can be identified by a user identifier ("UserID") that is unique at least within the user's respective organization. In some such implementations, each organization also has a unique organization identifier ("OrgID").

In some such implementations, each row of the Users Table represents a unique user. Each row can include an OrgID in a first column, a user identifier UserID in a second column, and various information about the user in one or more additional columns. For example, a third column can include an identification of a user type (for example, a standard user or a portal user), a fourth column can include the user's actual name or screen name, a fifth column can include the user's email address, and a sixth column can include a password. In some alternative implementations, these or additional columns can include other information about or pertaining to the users.

In some implementations, the Groups object is a data structure that can be represented or conceptualized as a "Groups Table" that associates groups to information about or pertaining to the respective groups including, for example, metadata about the groups. In some implementations, the Groups Table includes all of the groups within the organization. In some other implementations, there can be a Groups Table for each division, department, team or other sub-organization within an organization. In implementations in which the organization is a tenant of a multi-tenant enterprise social network platform, the Groups Table can include all of the groups within all of the organizations that are tenants of the multitenant enterprise social network platform. In some implementations, each group can be identified by a group identifier ("GroupID") that is unique at least within the respective organization.

In some such implementations, each row of the Groups Table represents a unique group. Each row can include an OrgID in a first column, a GroupID in a second column, and various information about the group in one or more additional columns. For example, a third column can include a group type (for example, an identification of whether the group is public or private), a fourth column can include a name or title of the group, a fifth column can include a UserID associated with the owner of the group (for example, the user that created the group), a sixth column can include information about the group (for example, a short description of a membership characteristic such as a purpose, objective or other relating quality of the members), and a seventh column can include a description of the group (for example, a longer description of the group's purpose or objective and membership characteristics). In some implementations, the information or description can include clickable or otherwise selectable textual or other user interface (UI) elements (for example, hyperlinks) that direct the user to the respective page associated with the selected element. In some alternative implementations, these or additional columns can include other information about or pertaining to the groups.

In some implementations, communities are stored as specialized groups within the Groups Table. In some other implementations, communities are stored in a separate Communities Table and have unique CommunityIDs.

In some implementations, the database system 16 includes a "Group-User relationship object." The Group-User relationship object is a data structure that can be represented or conceptualized as a "Group-User Table" that associates groups to users subscribed to the respective groups. In some implementations, the Group-User Table includes all of the groups within the organization. In some other implementations, there can be a Group-User Table for each division, department, team or other sub-organization within an organization. In implementations in which the organization is a tenant of a multi-tenant enterprise social network platform, the Group-User Table can include all of the groups within all of the organizations that are tenants of the multitenant enterprise social network platform.

In some such implementations, each row of the Group-User Table represents a defined relationship, association, link or subscription (all of which are used interchangeably herein where appropriate) between a particular group and users subscribed to the group. Each row can include an OrgID in a first column, a GroupID in a second column, and at least one UserID in one or more third columns. Thus, each row defines a subscription relationship in which a user identified by a UserID in the third column is subscribed to the group identified by the GroupID in the second column, and in which the group identified by the GroupID in the second column is within the organization identified by the OrgID in the first column of the same row. In some alternative implementations, additional columns can include other information about or pertaining to the subscriptions between the users and groups.

In some implementations, the Records object is a data structure that can be represented or conceptualized as a "Records Table" that associates records to information about or pertaining to the respective records including, for example, metadata about the records. In some implementations, the Records Table includes all of the records within the organization. In some other implementations, there can be a Records Table for each division, department, team or other sub-organization within an organization. In implementations in which the organization is a tenant of a multi-tenant enterprise social network platform, the Records Table can include all of the records within all of the organizations that are tenants of the multitenant enterprise social network platform. In some implementations, each record can be identified by a record identifier ("RecordID") that is unique at least within the respective organization.

In some such implementations, each row of the Records Table represents a unique record. Each row can include an OrgID in a first column, a RecordID in a second column, and various information about the record in one or more additional columns. For example, a third column can include a record type, a fourth column can include a name or title of the record and a fifth column can include the owner or creator of the record. In some alternative implementations, these or additional columns can include other information about or pertaining to the records.

In some implementations, the database system 16 includes a "Record-User relationship object." The Record-User relationship object is a data structure that can be represented or conceptualized as a "Record-User Table" that associates records to users subscribed to the respective records. In some implementations, the Record-User Table includes all of the records within the organization. In some other implementations, there can be a Record-User Table for each division, department, team or other sub-organization within an organization. In implementations in which the organization is a tenant of a multi-tenant enterprise social network platform, the Record-User Table can include all of the records within all of the organizations that are tenants of the multitenant enterprise social network platform.

In some such implementations, each row of the Record-User Table represents a subscription between a particular record and users subscribed to the record. Each row can include an OrgID in a first column, a RecordID in a second column, and at least one UserID in one or more third columns. Thus, each row defines a subscription relationship in which a user identified by a UserID in the third column is subscribed to the record identified by the RecordID in the second column, and in which the record identified by the RecordID in the second column is within the organization identified by the OrgID in the first column of the same row. In some alternative implementations, additional columns can include other information about or pertaining to the subscriptions between the users and records.

In some implementations, the database system 16 includes a "Feed Items object." The Feed items object is a data structure that can be represented or conceptualized as a "Feed Items Table" that associates users, records and groups to posts, comments, files or other publications to be displayed as feed items in the respective user feeds, record feeds and group feeds, respectively. In some implementations, the Feed Items Table includes all of the feed items within the organization. In some other implementations, there can be a Feed Items Table for each division, department, team or other sub-organization within an organization. In implementations in which the organization is a tenant of a multi-tenant enterprise social network platform, the Feed Items Table can include all of the feed items within all of the organizations that are tenants of the multitenant enterprise social network platform.

In some such implementations, each row of the Feed Items Table represents a defined relationship or link between a particular feed item and an associated user, record or group. Each row can include an OrgID in a first column, a FeedItemID in a second column, a UserID of the publishing user or owner of the feed item (for example, the user that submitted the publication associated with the feed item) in a third column, and a feed item body in a fourth column. That is, in some implementations, each row is associated with a particular feed item and the particular feed item is uniquely identified by the respective FeedItemID. The feed item body can include the content to be displayed in or with the feed item when displayed in a network feed. For example, the content in the feed item body can include the text of a publication submitted by the publishing user. The content in the feed item body also can include identifiers, links or addresses to separately stored documents, videos, images or other files or other publications to be displayed with the feed as part of the feed item. For example, in some implementations, the links to the files are displayed in the first hierarchical level of the feed item or a second hierarchical level of the feed item. In some other implementations, the files themselves (or a preview of the files) are displayed as part of the feed item.

In some implementations, other columns can include UserIDs, GroupIDs or RecordIDs of associated users, groups and records that have been @-mentioned by the publishing user as part of the publication. In some implementations, a ParentID can be specified in another column. The ParentID can include, for example, the UserID, RecordID or Group ID corresponding to the user feed, record feed or group feed where the publication was submitted. Another column can include a timestamp associated with a time the publication was submitted. Other columns can include text or links associated with feed-tracked updates to the feed item. Other columns can include the UserIDs of users that have "liked" the post, file or other publication in the feed item. Other columns can include the UserIDs of users that have shared the publication in the feed item.

Other columns of the Feed Items Table can include Comments identifying comments submitted on the publication and to be subsequently included in, for example, a second hierarchical level within the associated feed item when displayed in a network feed. In some such implementations, the database system 16 includes a "Comment Items object." The Comment Items object is a data structure that can be represented or conceptualized as a "Comment Items Table" that associates comments to associated feed items to which the comments were submitted (or "published"). In some implementations, the Comment Items Table includes all of the comments made by users within the organization. In some other implementations, there can be a Comment Items Table for each division, department, team or other sub-organization within an organization. In implementations in which the organization is a tenant of a multi-tenant enterprise social network platform, the Comment Items Table can include all of the comments within all of the organizations that are tenants of the multitenant enterprise social network platform.

In some such implementations, each row of the Comment Items Table represents a defined relationship or link between a particular comment and an associated feed item to which the comment was published. Each row can include an OrgID in a first column, a CommentID in a second column, a FeedItemID in a third column, a UserID of the publishing user that submitted the comment in a fourth column, and a Comment body in a fourth column. That is, in some implementations, each row is associated with a particular comment and the particular comment is uniquely identified by the respective CommentID. The comment item body can include the content to be displayed in or with the feed item when displayed in a network feed. For example, the content in the comment item body can include the text of a comment submitted by a publishing user. The content in the feed item body also can include links or addresses to separately stored files to be included in the comment when displayed in a network feed. For example, in some implementations, the links to the files are displayed in the comment, while in some other implementations, the files themselves (or a preview of the files) are displayed as part of the comment. In some implementations, other columns can include UserIDs, GroupIDs or RecordIDs of associated users, groups and records that have been @-mentioned by the published user in the comment.

Enterprise social network news feeds are different from typical consumer-facing social network news feeds (for example, FACEBOOK®) in many ways, including in the way they prioritize information. In consumer-facing social networks, the focus is generally on helping the social network users find information that they are personally interested in. But in enterprise social networks, it can, in some instances, applications, or implementations, be desirable from an enterprise's perspective to only distribute relevant enterprise-related information to users and to limit the distribution of irrelevant information. In some implementations, relevant enterprise-related information refers to information that would be predicted or expected to benefit the enterprise by virtue of the recipients knowing the information, such as an update to a database record maintained by or on behalf of the enterprise. Thus, the meaning of relevance differs significantly in the context of a consumer-facing social network as compared with an employee-facing or organization member-facing enterprise social network.

In some implementations, when data such as posts or comments from one or more enterprise users are submitted to a network feed for a particular user, group, record or other object within an online enterprise social network, an email notification or other type of network communication may be transmitted to all users following the respective user, group, record or object in addition to the inclusion of the data as a feed item in one or more user, group, record or other feeds. In some online enterprise social networks, the occurrence of such a notification is limited to the first instance of a published input, which may form part of a larger conversation. For instance, a notification may be transmitted for an initial post, but not for comments on the post. In some other implementations, a separate notification is transmitted for each such publication, such as a comment on a post.

IV. Automated Device Management

Various implementations relate generally to automated device management. In one innovative aspect, a device management system is configured to trigger and facilitate workflows to resolve exceptions detected in various devices managed by the device management system. The device management system maintains a prescription database storing prescriptions that define associated workflows for resolving particular exceptions. In some implementations, each prescription more particularly defines a respective action-oriented workflow including one or more automated steps for carrying out the prescription and resolving the exception. In some implementations, the device management system is generally configurable to receive device data associated with devices deployed by one or more organizations or by one or more enterprises or users associated with an organization. The device management system is further configurable to analyze the received device data and to detect the occurrences of exceptions based on the analysis. Responsive to the detection of an exception, the device management system determines whether the prescription database includes a prescription for the detected exception. Responsive to a determination that the prescription database includes a prescription, the device management system triggers a workflow defined by the prescription to resolve the exception. In some implementations, the workflow includes updating software or firmware installed in the device based on the prescription. In some implementations, the device management system is further configurable to trigger a second workflow in response to a determination that the prescription database does not include a prescription for the detected exception. In some such implementations, a prescription can then be generated by or in conjunction with the device management system based on analysis of the steps performed in the second workflow leading to the resolution of the exception.

In some implementations, some or all of the systems, databases or other components of the device management system can be implemented by a single- or multi-tenant database system such as the database system 16 described above with reference to FIGS. 1A and 1B. In some multi-tenant database implementations, the device management system manages devices owned, operated or deployed by the tenant organizations of the multi-tenant database system. In some such implementations, the device management system can be a platform, an application within a platform, or a feature within an application that the tenant organizations can purchase or subscribe to. Additionally or alternatively, the device management system can be configured to manage devices used by other enterprises or users associated with, but not within, a tenant organization of the database system. For example, such enterprises can include customers, suppliers, or service providers of a tenant organization. In some other implementations, the database system and the device management system within it can be owned or operated by an organization for managing devices used by customers, suppliers, or service providers associated with the organization.

In various implementations, the device management system can be configured to manage virtually any device deployed in the field, and in particular, any device that can be connected via a wireless or wired connection to a network enabling direct or indirect communication between the device and the device management system. In other words, the device management system can be configured to manage any network-accessible device usable or in use by an organization or another enterprise or user associated with the organization (for example, a customer of the organization). Some examples of devices that the device management system can manage include desktop computers, laptop computers, tablet computers, phone systems, smartphones, cellular phones, printers, copy machines, postal machines, servers, routers or other networking equipment, among other possible devices.

In various implementations, the devices (also referred to herein as "assets") deployed in the field are each identified by an asset identifier. As described above, in a multi-tenant database system implementation, each organization can be associated with an OrgID that uniquely identifies the organization within the database system 16. Each organization can create and maintain records facilitating the management of the organization and enterprises or other users that the organization deals with. Such records can include, for example, data objects representing and maintaining data for accounts (for example, representing a business relationship with another tenant organization, a third party enterprise or an individual consumer or other user). As described above, each record can be identified by a RecordID that is unique at least within the respective organization. Each record can be assigned a record type, which can be identified by a RecordTypeID. Examples of account record types include: customers, customer support, households (for example, individual consumers), partners, suppliers, and other organization types including organizations with whom no money is exchanged.

Figure 6:
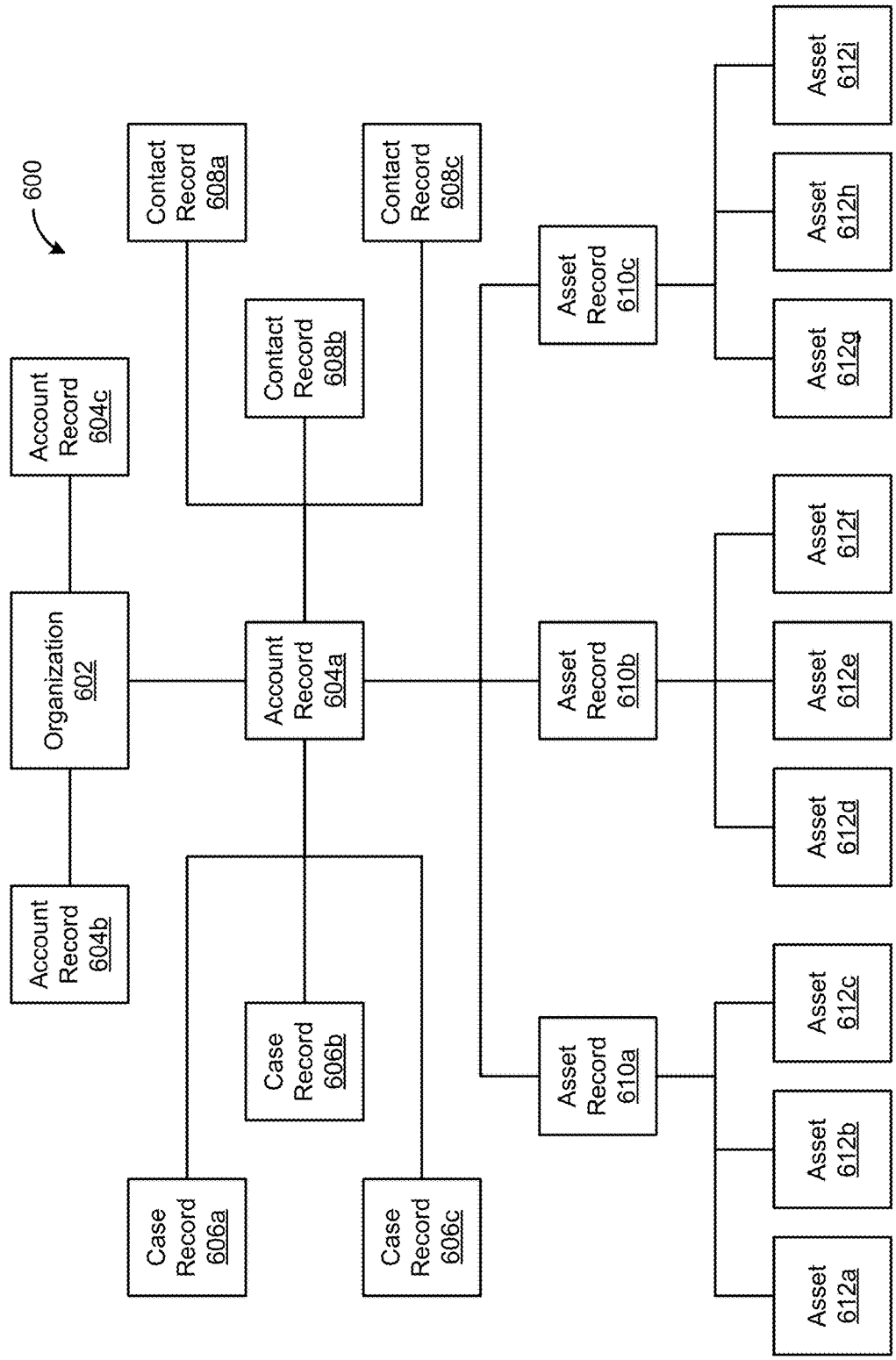
FIG. 6 shows a hierarchical representation of an example architecture for storing and associating records of an organization.

As described above, a record such as an account record can include or be associated with a number of lower level records or sub-records of other record types, for example, to facilitate the management of the account. For example, an account record can include or be associated with records such as cases, contacts, opportunities, leads, projects, contracts, orders, pricebooks, products, solutions, reports, forecasts and assets, among other possibilities. FIG. 6 shows a hierarchical representation of an example architecture 600 for storing and associating records of an organization. In the didactic example shown in FIG. 6, an organization is represented as a data object 602 within the database system 16. For example, the organization data object 602 can be stored in the tenant database 22 described above with reference to FIGS. 1A and 1B. In the illustrated example, the organization data object 602 includes or is associated with three account records 604a, 604b and 604c. The account record 604b includes or is associated with case records 606a-606c, contact records 608a-608c and asset records 610a-610c.

In some implementations, each of the asset records 610a-610c is associated with a particular type or category of assets. For example, asset record 610a can be a record identifying information associated with printers 612a-612c, asset record 610b can be a record identifying information associated with computers 612d-612f, and asset record 610c can be a record identifying information associated with mobile phones (for example, "smartphones"). Each asset included in an asset record can be identified by an asset identifier stored in the asset record. For example, the asset identifier can be a serial number of the asset (such serial numbers can be manufacturer-generated serial numbers or serial numbers created by the organization or the enterprise or user associated with the account). In some implementations, each asset record can include assets of one or more asset sub-types or classes. An asset sub-type can be used to identify or distinguish certain assets of a particular asset type from other assets within the same asset type. For example, printers 612a and 612b can be printers of a first model associated with a first asset sub-type identifier, and printer 612c can be a printer of a different model associated with a second asset sub-type identifier (for example, a different model provided by the same or a different manufacturer as the first model). As another example, computer 612d can be a laptop computer manufactured by a first manufacture and associated with a first asset sub-type identifier, computer 612e can be a laptop computer manufactured by a second manufacture and associated with a second asset sub-type identifier, and computer 612f can be a desktop computer manufactured by the first manufacturer and associated with a third asset sub-type identifier.

Figure 7:
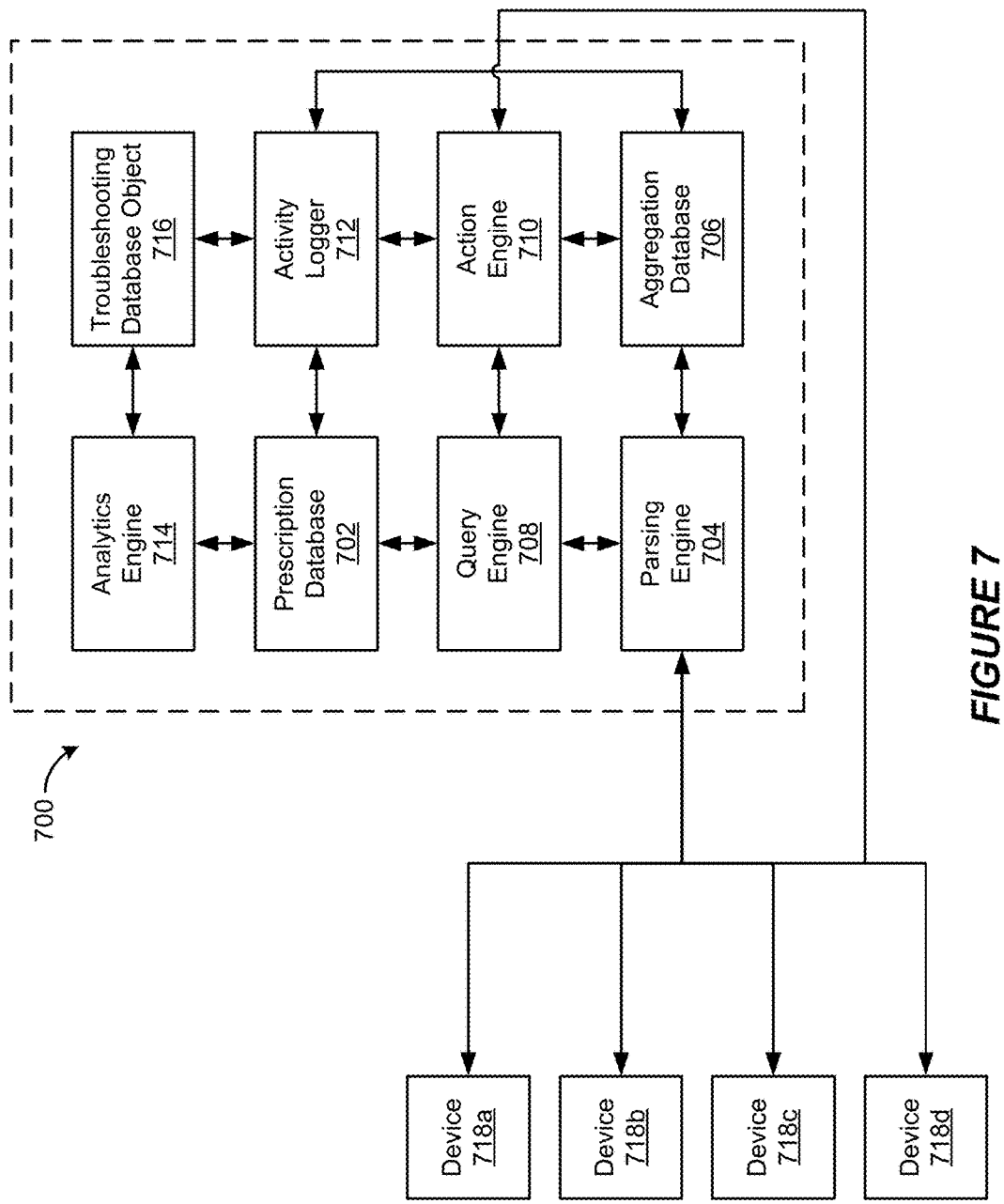
FIG. 7 shows a system diagram of example components of a device management system according to some implementations.

FIG. 7 shows a system diagram of example components of a device management system 700 according to some implementations. The device management system 700 includes a prescription database 702 storing prescriptions for remedying exceptions that can occur in the devices managed by the device management system 700. For example, the prescription database 702 can be implemented within the system database 24 or the tenant database 22 described above, or in a separate database. The device management system 700 also includes a parsing engine 704, an aggregation database 706, a query engine 708 and an action engine 710. In some implementations, the device management system 700 further includes an activity logger 712, an analytics engine 714 and a troubleshooting database 716.

In some implementations, an exception can generally be characterized as an action generated or performed by a device, or a result obtained by a device, that is exceptional, anomalous, irregular, inconsistent, unexpected or otherwise not part of normal operations or which conflicts with or departs from ordinary operational standards. In some implementations, the term exception is used interchangeably with anomaly, irregularity or error. Some such exceptions include device-detected exceptions for which the device generates an error code that it communicates to the device management system 700 automatically. In some other examples, the device may not be capable of detecting exceptions or may fail to detect that an exception has occurred. In such latter examples, the exception can be detected by the parsing engine 704 (as described in more detail below) based on data received by the parsing engine from the device. In other instances, a user of the device may detect the exception and cause the device to transmit a communication to the device management system 700 indicating that an exception has occurred, for example, by pushing or selecting an error button or help button (whether a physical button or a virtual button or other user interface element displayed in a display of the device). In some implementations, a user also can report an exception to the device management system 700 using another device, for example, using a mobile phone, laptop computer, desktop computer or other computing device.

In some other implementations, an exception can more broadly be characterized as any problem associated with a device including a problem experienced by a user in operating a device. In some such implementations, an exception can encompass a problem resulting from a user's lack of understanding in operating an otherwise properly working device. In such instances, the user can inform the device management system 700 of the problem or otherwise request help by pushing or selecting a help button on the device or by using another device (for example, a mobile phone, laptop computer, desktop computer or other computing device).

As described above, the prescription database 702 stores prescriptions for remedying exceptions encountered in devices managed by the device management system 700. In some implementations, the prescription database 702 is implemented within a larger knowledge database including informational articles, test results, device information, software information, firmware information, or other informational documents that can be accessed by the organization or by other enterprises or users affiliated with the organization. In some implementations, each prescription is stored as a data object in the prescription database 702. Each prescription defines a workflow for remedying one or more associated exceptions. In some implementations, the workflow is more specifically an action-oriented workflow including one or more automated steps for resolving (also referred to hereinafter as addressing, solving, remedying, fixing or correcting) an exception. In some implementations, the workflow also can include one or more semi-automated steps or one or more steps that require approval, authorization, verification, validation or investigation by one or more administrators, managers, technical support specialists or other authorized personnel, and in some implementations, steps that may require input from a user of the device. In some implementations, a workflow can include one or more embedded workflows each including a grouping or series of associated or integrated steps. For example, in some such implementations, one or more embedded workflows can require approval, authorization, verification, validation or investigation by one or more authorized personnel before proceeding to a next embedded workflow. In some such implementations, different embedded workflows can be managed, handled or facilitated by different personnel or different teams of personnel. In some implementations, each embedded work flow can be associated with a respective stage of an overarching grander workflow, or a status of a case record generated for the exception in the context of the overarching grander workflow.

In some implementations and use scenarios, a specialist working for or with the organization or the provider of the device management system 700 may have prior knowledge of the source of an anticipated or possible exception before the exception is every detected in any of the devices managed by the device management system 700. For example, a specialist may have prior knowledge of the source of an exception in a software program or in firmware from the manufacturer or provider of the software or firmware, from a manufacturer or provider of the device in which the software or firmware is installed, or from a technical blog, report, or some other knowledge source. In some such scenarios, the specialist or a team of specialists can write or otherwise generate a prescription for remedying the exception prior to the detection of the exception in any of the devices managed by the device management system 700. The prescription can then be stored in the prescription database 702 for use in resolving the exception when it is actually detected. In some other scenarios, a prescription can be created in response to resolving a previously-detected exception. Again, the prescription can then be stored in the prescription database 702 for use in resolving the same or a similar exception later detected in the same or a different device.

In the illustrated example, the parsing engine 704 is configurable to receive data from deployed devices 718a-718d, and to aggregate some or all of the received data in the aggregation database 706. As one of ordinary skill in the art will appreciate, while only four devices are shown in FIG. 7, the device management system 700 can be capable of managing hundreds or thousands or more devices. In some instances, the devices 718a-718d can be configured to periodically transmit data either directly or indirectly via one or more networks and networking devices to the device management system 700, and specifically, to the parsing engine 704. For example, the devices 718a-718d can be configured to transmit data collected since a last transmission on a daily, hourly or shorter time basis, or upon every power-up of the device or upon every awakening from a sleep state. Additionally or alternatively, the devices 718a-718d can transmit data when exceptions are detected by the devices or when polled or requested to transmit data by the device management system 700.

The parsing engine 704 also monitors and analyzes the aggregated device data. The parsing engine 704 is further capable of detecting exceptions in the devices based on the analysis. For example, the parsing engine 704 can detect exceptions based on the identification of actions, results or data that are exceptional, anomalous, irregular, inconsistent, unexpected or otherwise not part of normal operations or which conflict with or depart from ordinary operational standards.

Figure 8:
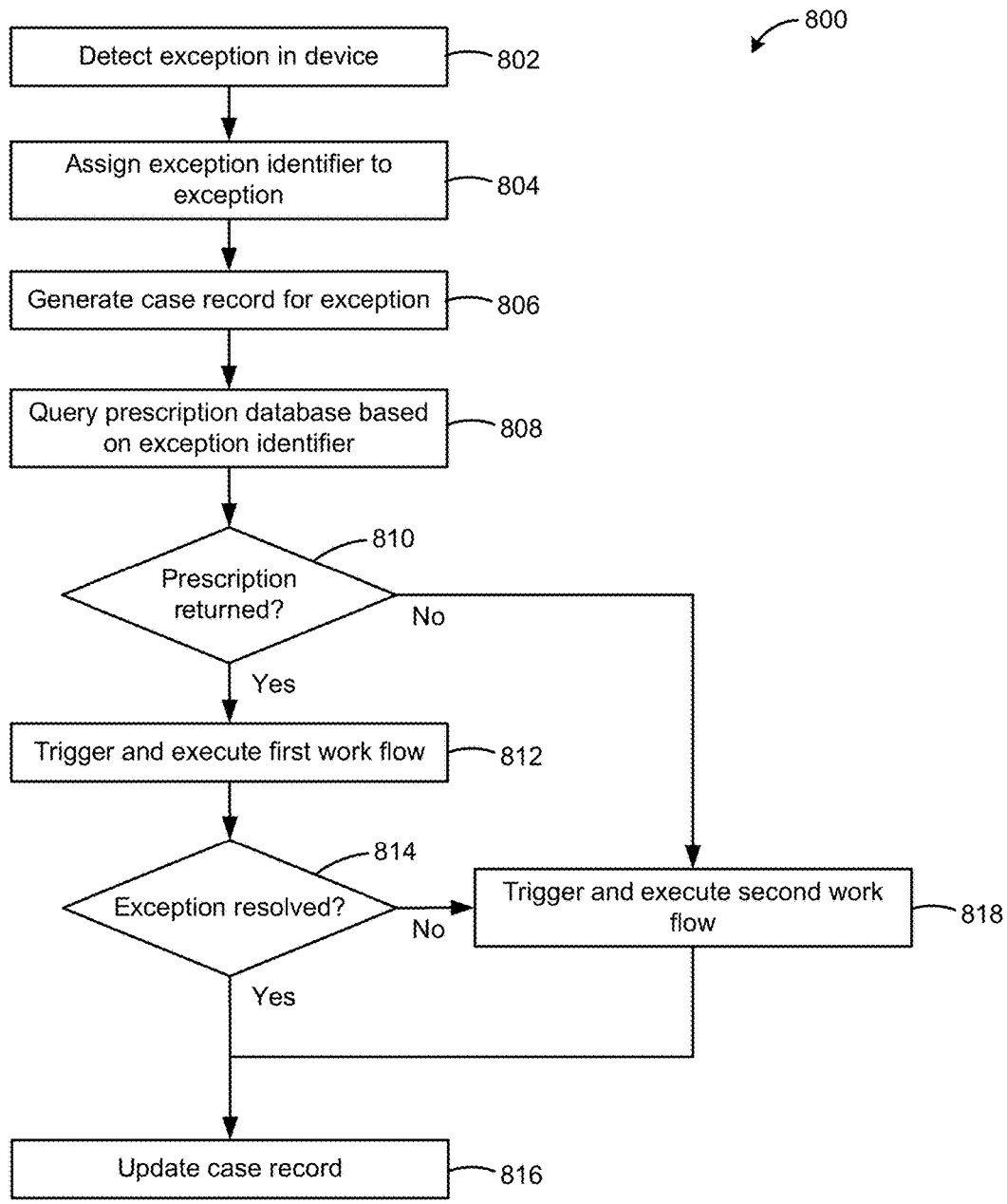
FIG. 8 shows a flow chart illustrating an example process for detecting and remedying an exception according to some implementations.

FIG. 8 shows a flow chart illustrating an example process 800 for detecting and remedying an exception according to some implementations. The process 800 begins in block 802 with the parsing engine 704 detecting an exception in a device. In block 804, the parsing engine 704 assigns, generates or receives an exception identifier for the detected exception. In some instances, an exception identifier can be an error code generated by the respective device experiencing, or that experienced, the detected exception. In such instances, the device can transmit the error code to the parsing engine 704, which can detect the exception in block 802 based on the identification of the received error code. The parsing engine 704 can then use the error code as the exception identifier for the exception in block 804.

As described above, the parsing engine 704 can additionally or alternatively detect an exception in block 802 through the analysis of the data received from the deployed devices. The parsing engine 704 can then assign or generate an exception identifier that identifies the exception in block 804. In some such implementations, the exception identifier can include some or all of the anomalous data. Additionally or alternatively, the exception identifier can include the asset identifier (for example, the serial number) of the device and a timestamp indicating when the exception was detected. The exception identifier also can include an identifier of the software, firmware or hardware element in which the exception occurred (if known).

Additionally, in instances in which the exception relates to a user's report of an exception or a user's lack of understanding in operating a device, the parsing engine 704 can detect the exception in block 802 based on the receipt of an error or help message generated in response to the user selecting an error or help button. Additionally or alternatively, the parsing engine 704 can detect the exception based on the receipt of repeated user input entries, repeated data results, repeated actions, or repeated series of such entries, data results or actions within a defined duration of time. Such repeated patterns can be used by the parsing engine 704 to determine that the user is having difficulty in operating the device.

In some implementations in which the parsing engine 704 assigns or generates the exception identifier for the detected exception, the parsing engine 704 can compare the data for the exception with data for previously-detected or otherwise known exceptions. For example, such previously-detected or otherwise known exceptions can be stored in a table, list or other data object along with associated exception identifiers. In some implementations, if the parsing engine 704 detects an exception that is identical or sufficiently similar to an exception in the exception table, the parsing engine 704 assigns to the new exception the appropriate (for example, best matching) exception identifier from the exception table. In some such implementations, if the parsing engine 704 detects an exception that is not in the exception table (for example, because it is a previously unencountered exception), the parsing engine 704 generates a new exception identifier for the new exception and adds the new exception identifier and the new exception data to the exception table.

In some implementations, responsive to the detection of an exception, the parsing engine 704 also generates, in block 806, a case record for the exception. In some other implementations, the parsing engine 704 can cause another application (for example, a CRM application) to generate the case record in 806. The parsing engine 704 generates the case record to include the exception identifier received, assigned or generated as described above in block 804. In some instances, the parsing engine 704 also includes the asset identifier for the device from which the exception was detected. In some implementations, the parsing engine 704 also identifies and includes in the case record an identifier of the owner of the device, and in some instances, an identifier of the user who was using the device at the time of the exception. For example, in instances in which the owner of the device is an organization that is a tenant of a multi-tenant database system, the owner identifier can be an OrgID. As another example, if the owner of the device is a customer of an organization, the owner identifier can be a RecordID such as an identifier of an account corresponding to the customer. In some implementations, the parsing engine 704 also can identify and include in the case record one or more of: a model number associated with the device, a hardware version associated with one or more hardware components of the device, a firmware version associated with firmware stored in the device, and software versions associated with software installed in the device. For example, the parsing engine 704 can identify such model or version information by accessing the asset record associated with the device. In some implementations, the case record also can include an audit trail of data aggregated by the parsing engine 704 for the device including data associated with user or device actions, activities or events leading up to the exception. In some implementations, the case record also can include one or more specialists, experts, managers, or other users responsible for performing, completing, supervising, or authorizing various steps or tasks in a workflow associated with the case record. Such information also can be obtained by accessing the associated asset record or the overlying account record. The case record also can include a physical location of the device as well as a network address of the device. Again, such information can be obtained by accessing the associated asset record.

In some implementations, the parsing engine 704 communicates a request, command or other instructive communication (hereinafter referred to collectively as a "request") to a query engine 708. The request includes the associated exception identifier for the detected exception, and in some instances, the asset identifier for the associated device from which the exception was detected (as described above, in some implementations, the exception identifier already includes the asset identifier). Responsive to the request from the parsing engine 704, the query engine 708 queries the prescription database 702 in block 808 for a prescription to remedy the exception.

Generally, the query engine 708 queries the prescription database 702 for prescriptions having or associated with the same exception identifier. In some implementations, the query engine 708 queries the prescription database 702 for a prescription having the same exact exception identifier. In some other implementations, the query engine 708 can query the prescription database 702 for one or more prescriptions associated with some or all of the information extracted from the exception identifier. For example, in implementations in which the exception identifier includes an error code, the query engine 708 can query the prescription database 702 for prescriptions associated with the same error code. Additionally or alternatively, in implementations in which the exception identifier includes anomalous data from which the exception was detected, the query engine 708 can query the prescription database 702 for prescriptions associated with the same anomalous data. Additionally or alternatively, the query engine 708 can query the prescription database 702 for prescriptions associated with the same asset identifier, the same asset sub-type identifier, the same asset type identifier, or the same asset record identifier.

In some such implementations, the query engine 708 can send multiple queries to the prescription database 702 or can send a single complex query to the prescription database. As an example of the former, the query engine 708 can send a first query associated with an error code identified in the exception identifier, a second query associated with anomalous data identified in the exception identifier, and a third query associated with the asset identifier, the asset sub-type identifier, the asset type identifier, or the asset record identifier. If more than one prescription is returned, the query engine 708 can prioritize the results to select the best-matching prescription. For example, a prescription associated with the same error code can be selected over a second prescription associated with the same asset record identifier. As another example, a prescription associated with both the same error code and the same asset identifier can be selected over a second prescription associated with just the same asset identifier. As an example of a single complex query, the query engine 708 can query the prescription database 702 for a prescription associated with the same exception identifier as well as the same asset identifier, the same asset sub-type identifier, the same asset type identifier, or the same asset record identifier.

In block 810, the query engine 708 receives the result(s) of the query and determines whether a prescription was returned. In some other implementations, the query engine 708 communicates the result(s) of the query to the action engine 710, which then determines, in block 810, whether a prescription was returned. In some implementations, the action engine 710 also can be configured to select a best-matching prescription if more than one prescription is returned in the results. If at least one prescription for the exception is found in the prescription database 702, the action engine 710 triggers a first workflow in block 812 associated with carrying out the prescription. As described above, the first workflow can be an action-oriented workflow including one or more automated steps, stages or blocks (hereinafter used interchangeably) for carrying out the prescription and resolving the exception. In some implementations, the workflow also can include one or more semi-automated steps or one or more steps that require approval, authorization, verification or validation by one or more administrators, managers, technical support specialists or other authorized personnel, and in some implementations, steps that may require input from a user of the device (such as an authorization, verification or response to a question).

When the first workflow is completed, the action engine 710 determines, in block 814, whether the exception has been resolved. In some other implementations, block 814 can be a final step in the workflow triggered and executed in block 812. In some implementations, resolving an exception can include remedying, updating, correcting, fixing, removing or bypassing the source or root cause of the exception. In some other implementations, resolving an exception can include communicating a set of instructions to a user or engaging the user in a live textual, graphical, audio or visual chat (whether using the device or using another device such as a mobile phone). Such implementations can be useful or desirable in instances in which the user was having difficulty in operating an otherwise properly functioning device.

If the exception has been resolved, the process 800 can conclude in block 816 with the action engine 710 updating the associated case record to indicate that the exception has been resolved. For example, the action engine 710 can update a status of the case record to a "closed" or "resolved" status. In some implementations, in response to such a status change of the record, the action engine 710 can then trigger a communication to a user indicating that the exception has been resolved. For example, the communication can be sent to the user who was operating the device at the time of the exception or to a manager or other authorized personnel responsible for ensuring that the exception was resolved.

In some implementations, in response to a determination in block 814 that the exception has been resolved, or in response to the updating of the case record in block 816, the action engine 710 then performs a research workflow to determine whether other similar assets should be updated based on the prescription. For example, the action engine 710 can identify other devices listed in the same asset record as the device from which the exception was detected. In instances in which the prescription workflow involved updating an older version of software or firmware to a new version, the action engine 710 can identify, or cause another application to identify, other devices in the asset record that have an older or unacceptable version of the same software or firmware. More specifically, the action engine 710 can access (or cause to be accessed) the corresponding asset record to identify the versions installed in the other devices in the asset record to determine whether the other devices could or should be updated to the new version. Similarly, in instances in which the prescription workflow involved applying a patch to the software or firmware, the action engine can identify, or cause to be identified, other devices that could or should be updated with the patch. Again, the corresponding asset record can provide information as to which of the devices have had the patch installed.

In some such implementations, if it is determined that one or more other devices should be updated based on the prescription, the action engine 710 can automatically trigger the application of the first workflow to each of the other devices. In this way, the other devices can be updated proactively to avoid the occurrence of the exception. In some implementations, a case record also can be opened for each of the other devices. For example, opening case records for the other devices can be useful or advantageous if the first workflow involves semi-automated or manual steps such as performances, authorizations, or verifications by tasked personnel. In some other instances, case records need not be opened for the other devices (for example, if the workflow is fully automated).

In some other implementations, while other devices can be eligible for the prescription (for example, if the other devices also have older or unacceptable versions), the action engine 710 may not automatically apply the prescription and trigger the associated workflow to some or all of the other eligible devices. For example, an administrator can opt in or opt out of the automatic triggering of the workflow for some or all of the devices managed by the device management system 700. In some such implementations, the action engine 710 can instead generate a list of the other devices and communicate the list to an administrator, manager or other authorized personnel. In such instances, the authorized personnel can determine whether or not to apply the prescription to each of some or all of the other devices in the list. For example, the authorized personnel can determine whether or not to apply the prescription to each of the other devices based on a severity of the exception (for example, based on whether the exception renders the device inoperative for some or all of its functions).

Other factors also can or may affect a determination to apply the prescription to the other devices whether such determination is made by the action engine 710 or by authorized personnel. For example, if there are only a small number of the other devices, the action engine 710 or the authorized personnel may determine to apply the prescription resulting in the triggering of the first workflow. On the other hand, if there are a large number of the other devices, the action engine 710 or the authorized personnel may determine not to apply the prescription, or alternatively, to schedule the first workflow at a later time (such as a time of day or day of week when the devices are not typically in use). As another example, the application of the prescription or the triggering of the associated workflow can be implemented in a staggered fashion. In some such implementations, the prescription can be applied to all of the devices at the same time, but the triggering of the associated workflow for various subsets of the devices can be staggered or scheduled to begin at different times. In other words, the application of the prescription does not necessarily trigger the associated workflow. For example, the workflow can be triggered in a first subset of the devices at a first time, triggered in a second subset at a second time, triggered in a third subset at a third time, and so on. Such staggering can ensure that not all of the devices are taken out of service or otherwise unavailable at the same time. Alternatively, it may be advantageous to apply the prescription to first subset of the devices to evaluate the success of the prescription before applying the prescription to a second subset of the devices. Other factors used in the determination can include the locations of the other devices. For example, the action engine 710 can trigger the workflow for devices in different time zones at the same time of day as opposed to at the same absolute time.

Generally, the action engine 710 selects, designs, generates or otherwise configures the workflow based on the prescription. In some implementations, an administrator of the organization (or an administrator of the device management system 700) can define a workflow or a rule set for defining a workflow using a rule builder application. One example of such a rule builder is the Lightning Process Builder provided by salesforce.com of San Francisco, Calif. In some implementations, each step of the workflow is defined and coded in the prescription. In some implementations, each step also is described in a human-readable or natural language representation in the prescription. This does not mean that the workflow triggered to carry out the prescription will necessarily be the same each time the workflow is used to resolve an exception associated with an exception identifier to which the prescription applies. For example, the action engine 710 may assign different personnel for different applications of the prescription to different devices or for different applications of the prescription to the same device at different times. For example, the personnel assigned to the associated case record for a given step in the workflow may depend on a physical location of the device or the availability of various personnel, among other factors.

As another example, while two devices can be associated with the same exception identifier and the same prescription (for example, because the devices produced the same error code or anomalous data), each of the devices may be different models of the same asset type or sub-type. In some such instances, the application of the workflow to the two devices can result in different steps, additional steps or various modifications to steps when carrying out the workflow in each of the two devices. In some other instances, while two devices may be identical and produce the same exception, unknowable or unpredictable variations in the devices may result in success of a step in the workflow for one device but failure of the same step in the same workflow for the other device (and thus may require one or more additional or different subsequent steps).

As another example, a workflow may include one or more determination steps or input steps that can change the next or remaining steps in the workflow based on a predetermined rule set included or defined in the prescription. For example, the workflow can include an initial step in which the action engine 710 accesses the account record associated with the device and identifies the version of a software program installed in the device. If the action engine 710 determines that the software version is the most current version, or at least an acceptable version, the action engine may then trigger a second action that can include, for example, executing a diagnostic test script. On the other hand, if the action engine 710 determines that the software version is not acceptable, the action engine may then trigger an action that includes updating the software program to a new version before proceeding to the step in which the diagnostic test script is executed.

Building on the last example, a workflow can generally include a first step or embedded workflow for performing an action with respect to the device. Based on an outcome of the action, the action engine 710 can trigger one of a set of second steps or second embedded workflows. In other words, the next step in a workflow can be based on a result (or combination of results) obtained in one or more previous steps in the workflow. For example, the action engine 710 can trigger a second step or second embedded workflow within a larger workflow based on the result obtained after performing one or more actions (such as the installation of an update or the execution of a diagnostic test script). In some other implementations or instances, the performance of one or more actions can result in the detection of a second exception. In such instances, the process 800 can proceed back to 804 with assigning an exception identifier to the second exception and querying the prescription database 702 for a second prescription based on the second exception identifier. If a second prescription is returned, the action engine 710 can then trigger a second workflow based on the second prescription. However, in instances in which a prescription for the second exception identifier wasn't returned, the action engine 710 can trigger a different second workflow as described in more detail below with reference to block 818 of FIG. 8.

In some implementations, the action engine 710 can select or generate the first workflow for the prescription returned in block 810 based on a type or category of the prescription. For example, a first prescription type can be associated with a software update, a second prescription type can be associated with a firmware update, a third prescription type can be associated with a software patch, a fourth prescription type can be associated with a firmware patch, a fifth prescription type can be associated with a virus removal operation, a sixth prescription type can be associated with an adjustment or reset of settings, and a seventh prescription type can be associated with a hardware fix or replacement. In other words, in some implementations or instances, a workflow to update a first software program based on a first prescription can be the same as or similar to a workflow to update a second software program based on a second prescription (for example, except for the fact that different software programs or updates will need to be installed). Similarly, a workflow to remove a first virus based on a first prescription can be the same or similar to a workflow to remove a second virus based on a second prescription (for example, because the same virus removal script can be used to remove each of the two viruses). In some such implementations, a rule set for implementing a workflow can be shared in multiple (similar or related) prescriptions as opposed to defining a workflow for each of the similar prescriptions in the respective prescription data objects. In some such implementations, each of the related prescriptions that include the same rule set in a coded form. In some other implementations, each of the related prescriptions can include an identifier or link to the rule set, which also can be stored in the prescription database and called when applying one of the related prescriptions. While the related prescriptions can include the same rule set, each of the related prescriptions also can include a file, a link to a file, or an identifier of a file that is different than in the other related prescriptions. As such, the workflows triggered and executed in carrying out the related prescriptions will be similar but will include installing or executing different respective files.

Additionally, in some implementations or use scenarios, workflows for some different types of prescriptions and some different exceptions also can be similar. For example, prescriptions associated with resolving exceptions associated with errors, "bugs," viruses, vulnerabilities or erroneous settings in software or firmware can involve similar workflows. In other words, while the sources of such exceptions may differ, and while one or more specialists tasked with authorizing, completing, or confirming one or more steps in the workflows may differ, the general steps of the workflows for carrying out the prescriptions or otherwise resolving the exceptions can be similar in some instances. More specifically, some such workflows can generally include a step, series of steps or embedded workflow for updating the device from which the exception was detected. In some instances, updating the device can include updating software or firmware installed in the device. Updating the software or firmware can include installing a new version of the software or firmware, installing a patch to correct an error, bug or vulnerability in the software or firmware, or executing a script to correct various settings. In some other scenarios, updating the device can include executing a virus removal script.

In some such implementations, the associated prescription can include a file containing the new version, the patch, the settings script or the virus removal script. For example, the file can be stored in the prescription database 702 in the same data object as the prescription. In some other implementations, the prescription can include a link to the file (such as a URL or other identifier of a source where the file is stored). In some such implementations, the file can be stored separately in the prescription database 702 and linked with one or more prescriptions (for example, because multiple prescriptions can include installing or executing the same file). In some other implementations, the file can be stored in a different database, for example, a different database within the device management system 700, a database outside of the device management system 700 but within the database system 16, or a database or other source external to the database system 16 (for example, in a location provided by a manufacturer or provider of the file such as a software manufacturer or vendor).

In some implementations, some of the above-described prescriptions also can include a file, or a link to a file, that includes a diagnostic test script. In such instances, the first workflow also can include a step in which the diagnostic test script is loaded into and executed by the device to determine whether the new version, patch, settings script, or virus removal script was successful in resolving the exception. For example, the diagnostic test script can be executed in block 814 described above to determine whether the exception has been resolved. In some other implementations, the associated workflow can include a step in which the user of the device (when the exception was detected) is requested to indicate whether the exception has been resolved in block 814.

In some other implementations, a prescription can include a diagnostic test script that can be loaded into and executed by a device for use in identifying the source of the exception. For example, the diagnostic test script can be loaded into and executed by the device in an initial or early step or stage of the first workflow (for example, prior to updating software or firmware, running any other scripts, or tasking one or more specialists to either physically access the device or access the device over a network). For example, the diagnostic test script can cause the device to perform a self-test routine. As another example, the diagnostic test script can cause the device to return a version of the device's firmware or a version of a software program. This can be useful if there is no version information in the asset record, or if there is a conflict between the actual version in the device and the version identified in the asset record.

Additionally, in some implementations, one or more tasked personnel can access the device by way of a canvas application that works in conjunction with an application programming interface (API) enabling the tasked personnel to virtually inspect the device, for example, to examine version information, to identify various settings, or to inspect other data.

In some instances, the transmission, installation or execution of a file, such as an update, patch or script, can be automatic and immediate based on a command from the action engine 710. In some other instances, one or more of the transmission of the file, the installation of the file, or the execution of the file can require approval or authorization by a specialist or manager. For example, prior to the performance of a step in the workflow that includes the transmission, installation or execution of a file, the workflow can include a step for obtaining approval or authorization by authorized personnel tasked with the responsibility for providing such approval or authorization. In some other implementations, the transmission, installation or execution of a file can be scheduled to be performed at a specified time or range of time, or scheduled to be performed based on the occurrence or performance of one or more other actions or the attainment of one or more results. For example, it may be desirable to perform an update during a time when the device is typically not in use (such as at night), when the device is in a sleep mode or other low-power or non-use state, or upon the device being rebooted or otherwise powered on.

As described above, an administrator of an organization can customize the rule sets defining how various workflows are implemented, for example, which users are tasked, which updates are available for which devices, and when such updates should be scheduled. In some implementations, an administrator also can, for each device (or for each asset type or sub-type) opt in or opt out of the sending of device data to the parsing engine 704, opt in or opt out of having updates or other files automatically communicated to, installed or executed by the device, or more generally opt in or opt out of management by the device management system 700. For example, an administrator can elect to allow only certain devices to transmit data automatically to the parsing engine 704 for security, confidentiality or privacy reasons. As another example, an administrator can elect to allow only certain types of data to be transmitted automatically to the parsing engine 704 (for example, the administrator can prevent the sending of personal, confidential or private data). As another example, an administrator can elect to allow only certain devices to be automatically updated by the action engine 710 for security, confidentiality or privacy reasons.

In some such implementations, the administrator of an organization can customize the management (such as the sending and aggregation of data or the automatic installation or execution of files) of various devices by the device management system 700 based on social trust profile settings configured by the administrator. Similarly, in some implementations, an administrator or other authorized employee or consumer that is a customer of (or otherwise deals with) an organization, can customize the management of various devices by the device management system 700 based on social trust profile settings. For example, a consumer that is a customer of an organization can customize what if any personal data associated with a device can be made available to a third party (that is, an entity other than the consumer, the organization and the operator of the device management system). For example, the consumer can customize what if any personal data associated with a device can be made available to the manufacture of the device, the provider of the device, the licensor of software installed on the device, the provider of a service associated with the device, or any customers or other fourth parties associated with the third party. More detailed processes and additional processes for implementing social trust profile settings can be found in U.S. patent application Ser. No. 14/145,735, now U.S. Patent Application Publication No. 2014/0115004, titled SYSTEMS AND METHODS OF AUDIT TRAILING OF DATA INCORPORATION and filed on 31 Dec. 2013, which is hereby incorporated by reference herein in its entirety and for all purposes.

Returning back to the process 800 of FIG. 8, if no prescriptions for the exception are found in the prescription database 702 in block 810, or if the action engine 710 determines that the exception has not been resolved in block 814, the action engine 710 triggers a second workflow in block 818. In some implementations, the second workflow is a non-prescription-based workflow. In some other implementations, the second workflow can be based on a default or general prescription accessed when no matching prescription is found in the prescription database 702. The second workflow can generally be used to resolve any exception but may require manual or semi-automated steps performed by or in conjunction with one or more authorized personnel as opposed to being fully or mostly automated. The second workflow generally includes identifying a source of the exception, determining a solution, and resolving the exception based on the solution. As with the first workflow, the second workflow also can be an action-oriented workflow including one or more automated steps such as loading and executing a diagnostic test script in an initial or other early step or stage in the second workflow. The second workflow also generally includes one or more steps or one or more steps that require investigation, testing, collaboration, approval, authorization, verification or validation by one or more administrators, managers, technical support specialists or other authorized personnel, and in some implementations, steps that may require input from a user of the device.

In some implementations, the second workflow can include a step of tasking, by the action engine 710, one or more technical support specialists to investigate the exception. For example, a technical support specialist can be tasked by associating a user identifier of the specialist (for example, a UserID) with the associated case record generated for the exception. In some implementations, in response to being tasked by the action engine 710, the action engine or another application then transmits a message to the technical specialists, for example, a social networking message, a text (for example, SMS) message, a multimedia (for example, MMS) message, or an email. In some implementations, some of the prescriptions can be assigned to or associated with one or more topics (for example, a particular software program or a particular asset type or sub-type). In some such implementations, various personnel tasked for the associated workflow can be tasked based on badging. For example, personnel can be badged with a particular topic when identified as a specialist or expert on the topic.

The second workflow also can include a step or embedded workflow in which one or more tasked personnel carry out the investigation, a step or embedded workflow in which the same or different tasked personnel collaborate with one another to determine a source or cause of the exception, a step or embedded workflow in which the same or different tasked personnel determine a solution for the exception, and a step or embedded workflow in which the same or different tasked personnel apply the solution to resolve the exception. For example, the second workflow can include one or more steps or embedded workflows that include traveling to a physical location of the associated device, accessing the device over a network, executing a diagnostic test script on the device, installing an update on the device, collaborating with other tasked personnel (for example, via a social network such as Chatter provided by salesforce.com of San Francisco, Calif.), and otherwise participating in the resolution of the exception.

In some implementations, the tasked personnel can be "swarmed" to the case record and collaborate to resolve the exception in a community setting or using a social networking feed as described above. In some implementations, the action engine 710 is configured to automatically subscribe or unsubscribe various users (such as specialists or managers) based on a change in a state or status of the case record. In some implementations, communications of information of or about the case record are automatically distributed to the subscribed users. In some implementations, the users that are automatically subscribed to the record are users that have a role in developing or working with the record in the case record's current status, or a role in transitioning the case record from its current status to another status. In some implementations, each stage or embedded workflow within a larger workflow can be associated with a particular state or status of the case record. In such implementations, it can be desirable for different users to be subscribed to the case record to receive updates or notifications concerning the case record at the different stages of the workflow. For example, some users may have active roles in resolving the exception for which the case record was created during one stage but may have no part in resolving the exception at other stages of the workflow. More detailed processes and additional processes for automatically subscribing and unsubscribing users to or from a record can be found in U.S. patent application Ser. No. 14/221,678, now U.S. Patent Application Publication No. 2014-0289272, titled AUTOMATICALLY SUBSCRIBING USERS OF AN ENTERPRISE NETWORK TO A RECORD and filed on 21 Mar. 2014, which is hereby incorporated by reference herein in its entirety and for all purposes.

In some implementations, the second workflow also includes creating a troubleshooting data object in the troubleshooting database 716 for recording data associated with steps performed by the tasked personnel in attempting to resolve the exception. For example, the action engine 710 can create the troubleshooting data object or cause another application (for example, the activity logger 712) to create the troubleshooting data object. The troubleshooting data object can be created for, and identified by, the associated exception identifier. The troubleshooting data object includes a log of data logged or acquired by the activity logger 712. In some implementations, the activity logger 712 logs all or substantially all activities associated with the performance of each step in the second workflow including automated, semi-automated or manual steps. In some implementations, the activity logger 712 logs successful steps or steps that lead to the resolution of the exception as well as unsuccessful steps or steps that do not directly lead to the resolution of the exception. For example, the activity logger 712 can log data associated with transactions or communications of data or files to or from the device and the action engine 710, communications among personnel tasked with performing one or more steps in the second workflow, as well as actions performed by the action engine 710, actions performed by the device, or manual or semi-automated actions performed by tasked personnel (whether over a network or via physical interaction with the device). As described above, such steps can include diagnostic or investigatory steps, steps involving the installation or execution of files, as well as collaborative steps. In other words, the activity logger 712 can capture the second workflow in its entirety in the form of a prescription attempt audit trail that can conclude with the resolution of the exception.

In some implementations, when it is determined that the exception is resolved, the activity logger 712 stops logging data for the second workflow and the troubleshooting data object (at least for the currently resolved exception). However, in some implementations, the parsing engine 704 continues to aggregate data from the device during the second workflow as well as after the second workflow is completed. Similarly, the parsing engine 704 also can continue to aggregate data from the device during the first workflow as well as after the first workflow has been completed. Indeed, in some implementations, the activity logger 712 may obtain the data it logs from the data aggregated by the parsing engine 704. In some other implementations, the activity logger 712 can receive data directly from the action engine 710, directly from the device, directly from tasked personnel, or via updates or additions to the case record.

In some implementations, the troubleshooting data object includes a number of rows, where each row can include a step, an activity within a step or a result of a step (for example, a data result, an indication of whether the step was successful, or an identification of a second exception identifier obtained after executing the step). In some implementations, the rows in the troubleshooting data object are arranged in chronological order. For example, a timestamp can be associated with each activity, step, or result. In some implementations, the troubleshooting data object can include logged activity data across all managed devices and over all time; that is, the troubleshooting data object can include logged activity data associated with the performances of workflows for resolving all exceptions having the same exception identifier.

In some implementations, analysis of the troubleshooting data object can then be used to generate a new prescription for exceptions having the same or a similar exception identifier. In some implementations, an analytics engine 714 performs analytics such as correlative analysis on the data logged in the troubleshooting data object. In some implementations, the analytics engine 714 can be capable of automatically generating the prescription and defining the associated workflow or rule set. For example, in implementations in which the troubleshooting data object includes data for a plurality of workflows used to resolve the same or similar exceptions, the analytics engine 714 can correlate the data for each of the logged workflows to determine a prescription workflow. In some implementations, the analytics engine 714 also can correlate data from multiple troubleshooting data objects to create one or more prescriptions for one or more exceptions. For example, various knowledge-centered support (KCS) methodologies, practices or processes as well as machine learning systems or processes can be used to develop the prescriptions.

Additionally or alternatively, the data logged in the troubleshooting data object can be evaluated by one or more specialized personnel. For example, a specialized personnel can refine the prescription generated by the analytics engine 714 to make it more efficient (for example, by removing unnecessary steps) or to modify it to generate other prescriptions for similar exceptions. In some other implementations, the specialized personnel can modify the prescription generated by the analytics engine 714 to add one or more additional steps, for example, steps for obtaining approval, authorization, validation, verification or confirmation before proceeding to a next step or next stage in the workflow.

Similarly, the specialized personnel also can modify the prescription generated by the analytics engine 714 to add one or more security features. For example, some prescriptions in the prescription database 702 can be configured to include one or more steps that require human intervention to ensure security. Such human intervention can be used as checkpoints to ensure that the workflow is an authorized workflow and not a workflow triggered by a scrupulous third party. For example, a tasked personnel may be required to use a password, a certificate or a combination of both to perform or authorize a next step in the workflow. In some implementations, authorized personnel can be required to carry a hardware token or dongle (for example, an RSA SecurID token) that they use to access the device or to perform a step in the workflow. In some other implementations, the action engine 710 can generate a digital security token (a "soft token"). For example, where a next step in the workflow is an installation or execution of an update, script or other file, the security token (whether digital or physical) can have an expiration date after which the file is no longer permitted or authorized to be installed.

Figure 9:
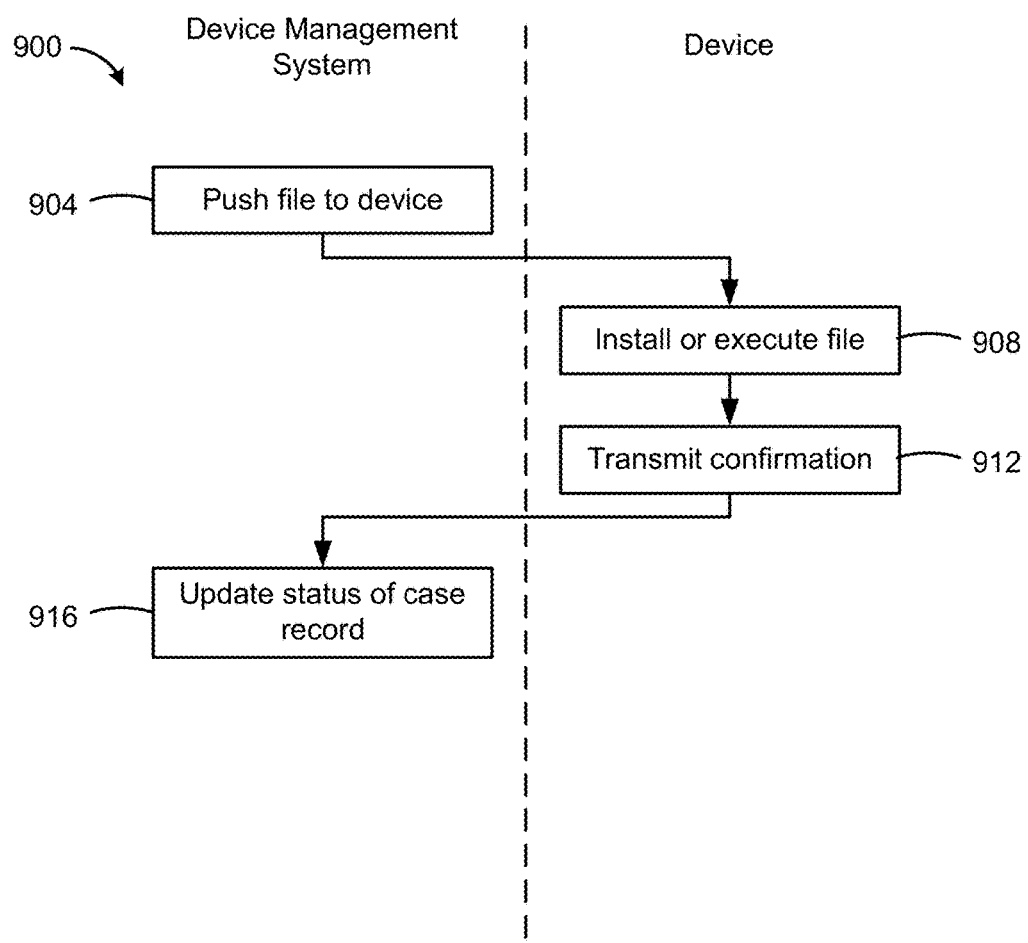
FIG. 9 shows an example automated workflow for carrying out a prescription according to some implementations.

FIG. 9 shows an example automated workflow 900 for carrying out a prescription according to some implementations. For example, the workflow 900 can implement some or all of block 812 of FIG. 8. In some implementations, the workflow 900 is more particularly associated with a prescription for updating software or firmware installed in a device. In some other implementations, the workflow 900 is more particularly associated with a prescription for removing a virus installed in the device. In some other implementations, the workflow 900 is more particularly associated with a prescription for adjusting or resetting settings in the device. The workflow 900 begins in block 904 with the action engine 710 pushing a file (included in or linked to the prescription) to the device over one or more networks. As described above, depending on the particular prescription, the file can contain a new version or a patch for software or firmware installed on the device, a virus removal script for removing a virus installed in the device, or a script to adjust or reset settings in the device, among other possibilities.

In response to receiving the file, the device automatically installs or executes the file in block 908. In some implementations, after the installation or execution of the file, the device automatically transmits a confirmation that the file was successfully installed or executed to the device management system 700 in block 912. In various implementations, the confirmation can be received by the action engine 710 or received by the parsing engine 704 and then forwarded to the action engine 710. In some implementations, in response to receiving the confirmation, the action engine 710 then updates, in block 916, a status of the associated case record to reflect the confirmation. For example, the action engine 710 can update the status of the case record to a "closed" status or a "resolved" status. In some implementations, the action engine 710 also updates the case record to indicate what file was installed or executed and when it was installed or executed. For example, the action engine 710 can include a version identifier identifying a new version of the software or firmware, a patch identifier identifying a patch, or a description indicating that a virus removal script was executed (and possibly what viruses were removed) or that the settings were adjusted or reset (and what the settings current are after the adjustment).

Figure 10:
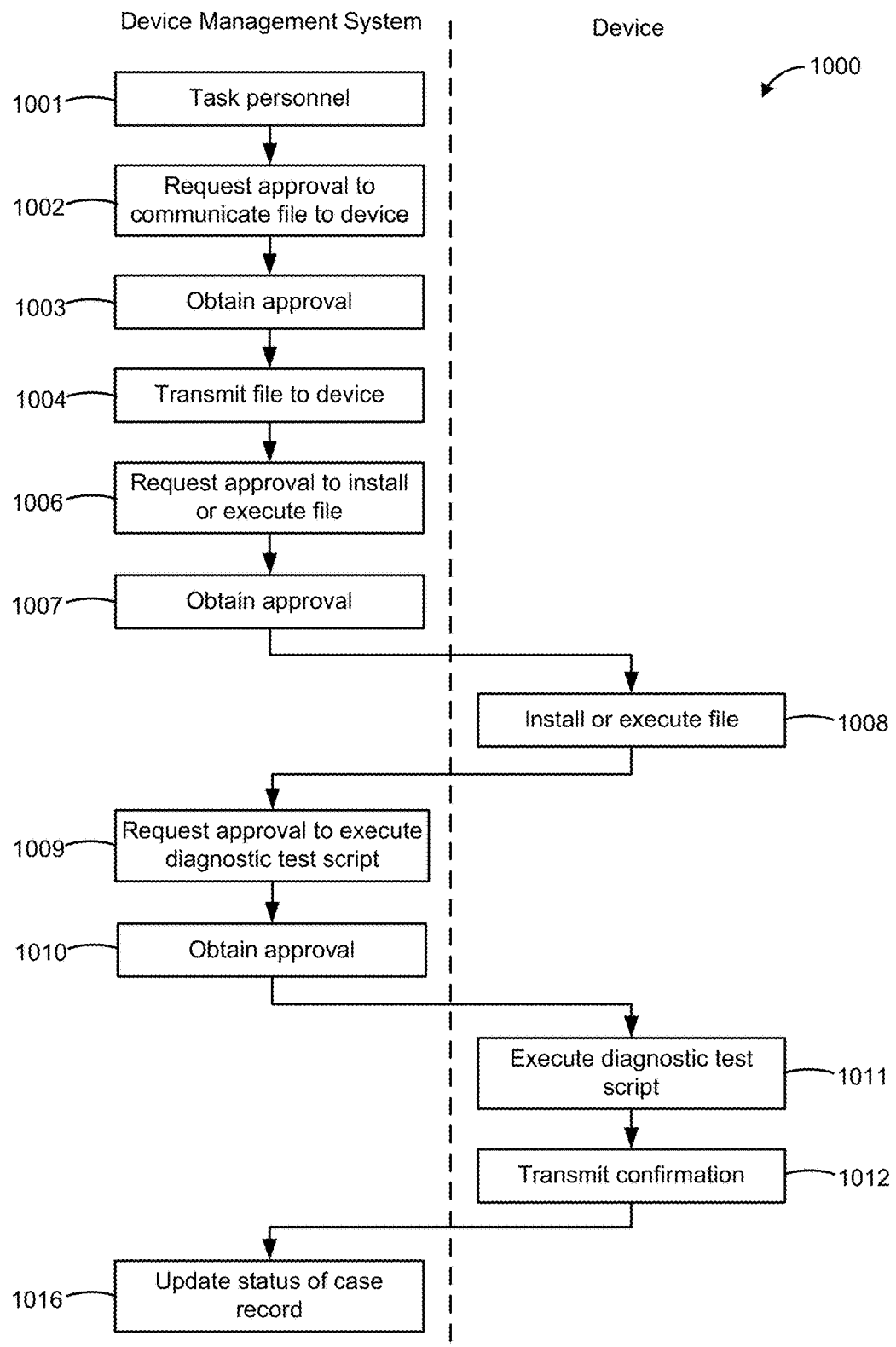
FIG. 10 shows an example semi-automated workflow for carrying out a prescription according to some implementations.

FIG. 10 shows an example semi-automated workflow 1000 for carrying out a prescription according to some implementations. For example, the workflow 1000 can implement some or all of block 812 of FIG. 8. In some implementations, the workflow 1000 is similar to the workflow 900 except for the addition of or modification of one or more blocks. For example, various steps in the workflow 1000 can require approval before commencement (thus the characterization of "semi-automated").

The workflow 1000 begins in block 1001 with the action engine 710 tasking one or more first personnel. As described above, in some implementations, various different personnel can be tasked at different stages of the workflow 1000. In some implementations, in block 1002, the action engine 710 requests approval from one or more of the tasked personnel to communicate a file in the prescription to the device. For example, the tasked personnel can indicate the authorization via a user interface on the device. In some other implementations, the action engine 710 can push a message to the tasked personnel at another device, for example, a mobile phone, computer or other computing device, requesting the authorization. In bock 1003, the action engine 710 obtains the requested approval, and in block 1004, transmits the file to the device. In some implementations, instead of the device automatically installing or executing the file as in block 908 of the workflow 800, the device does not install or execute the file until receiving authorization. For example, the action engine 710 (or the device) can request approval to install or execute the file in block 1006. In bock 1007, the action engine 710 (or the device) obtains the requested approval, and in block 100, the device installs or executes the file.

In some implementations, the action engine 710 then requests, in block 1009, approval to transmit (or approval to cause the device to execute) a diagnostic test script. In block 1010, the action engine 710 obtains the approval, and responsive to the approval, the device is instructed or permitted to execute the diagnostic test script in block 1011. In some implementations, after the execution of the test script, the device automatically transmits a confirmation that the test script was executed to the device management system 700 in block 1012. In various implementations, the confirmation can be received by the action engine 710 or received by the parsing engine 704 and then forwarded to the action engine 710. In some implementations, in response to receiving the confirmation, the action engine 710 then updates, in block 1016, a status of the associated case record to reflect the confirmation. For example, the action engine 710 can update the status of the case record to a "closed" status or a "resolved" status. In some implementations, the action engine 710 also updates the case record to indicate what file was installed or executed and when it was installed or executed. For example, the action engine 710 can include a version identifier identifying a new version of the software or firmware, a patch identifier identifying a patch, or a description indicating that a virus removal script was executed (and possibly what viruses were removed) or that the settings were adjusted or reset (and what the settings current are after the adjustment).

Figure 11:
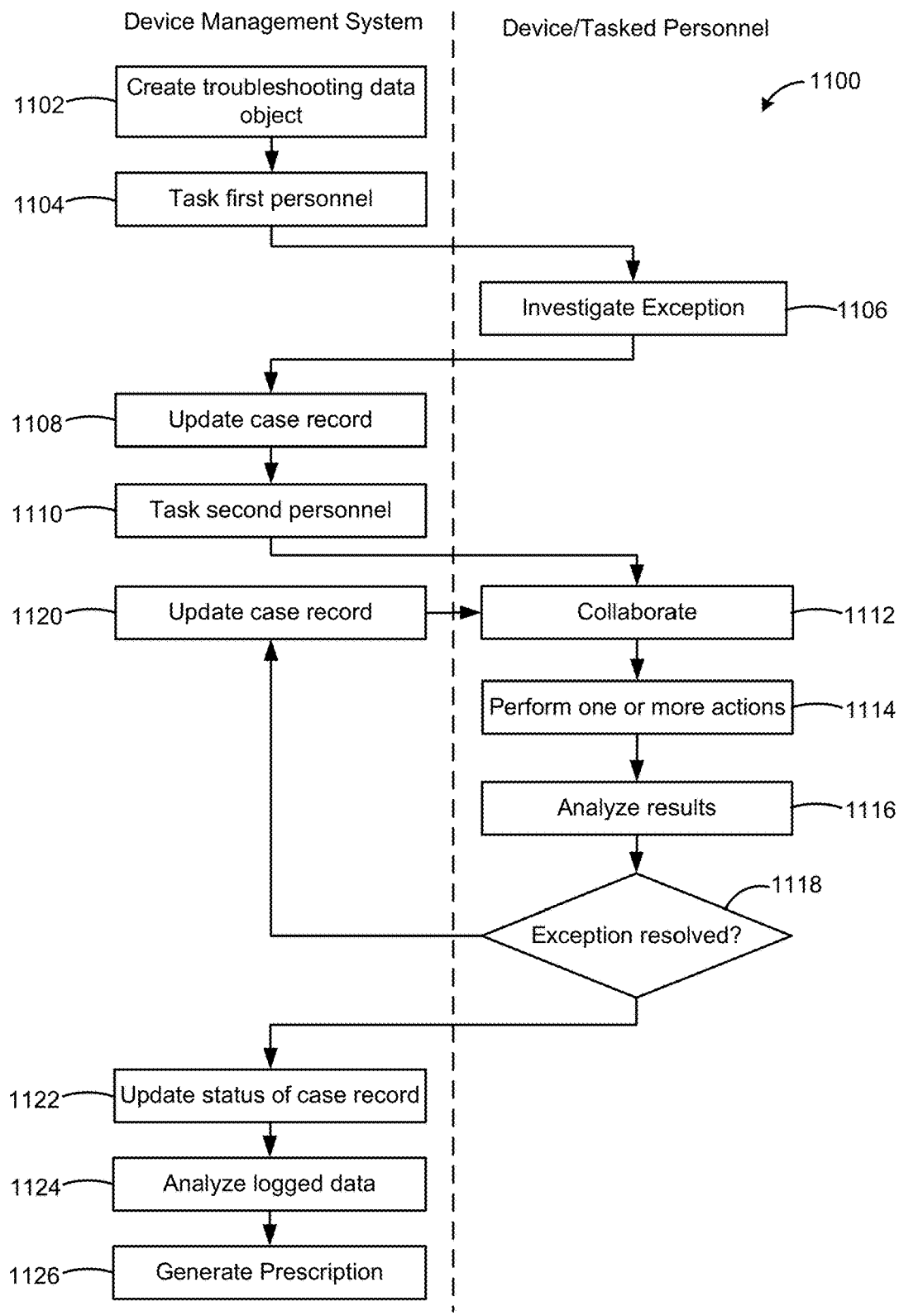
FIG. 11 shows an example workflow for resolving an exception for which no prescription is available according to some implementations.

FIG. 11 shows an example workflow 1100 for resolving an exception for which no prescription is available according to some implementations. For example, the workflow 1100 can implement some or all of block 818 of FIG. 8. In some implementations, the workflow 1100 begins in 1102 with the action engine 710 creating or accessing a troubleshooting data object. In block 1104, the action engine 710 tasks one or more first personnel. As described above, in some implementations, various different personnel can be tasked at different stages of the workflow 1100, and in some implementations, based on different states or status updates to the associated case record. In block 1106, the tasked first personnel investigate the exception. As described above, investigating the exception can include traveling to a physical location of the associated device, accessing the device over a network, executing a diagnostic test script on the device, or performing other investigative techniques or steps. In block 1108, the case record is updated based on the results of the investigation.

Responsive to the update in block 1108, the action engine 710 then tasks one or more second personnel. In block 1112, the second personnel collaborate to find a solution to the exception. For example, the tasked second personnel can collaborate via a social network such as Chatter provided by salesforce.com of San Francisco, Calif.). In block 1114, the second personnel perform (or cause the device to perform) one or more actions, for example, installing or update various files, executing various tests or scripts, or adjusting various settings. In block 1116, the second personnel analyze the results of the actions in block 1114. For example, the results can generally include results generated and displayed or otherwise conveyed by the device. In some implementations, the second personnel analyze the results in block 1114 in conjunction with the action engine 710. For example, some of the results or some of the analysis can be performed by the action engine 710. In block 1118, the tasked second personnel determine whether the exception has been resolved. Again, in some implementations, the second personnel make the determination in block 1118 based on determinations or results made and provided by the action engine 710 or the device.

If it is determined that the exception has not been resolved, the action engine 710 can update the case record in 1120 to reflect the attempts. In some implementations, the workflow then proceeds back to block 1112. On the other hand, if it is determined that the exception has been resolved, the action engine 710 can update a status of the case record in block 1122 to reflect the successful resolution. In some implementations, the action engine 710 also updates the case record to indicate what, if any, file was installed or executed and when it was installed or executed. For example, the action engine 710 can include a version identifier identifying a new version of software or firmware, a patch identifier identifying a patch, or a description indicating that a virus removal script was executed (and possibly what viruses were removed) or that the settings were adjusted or reset (and what the settings current are after the adjustment).

As described above, throughout the workflow 1100, the activity logger 712 can be logging data associated with the performance and results of the actions performed, and storing this data in the troubleshooting data object. In some implementations, the workflow 1100 then proceeds with the analytics engine 714 performing analysis of the logged data in block 1124 and generating a new prescription for the exception in block 1126.

As one of ordinary skill in the art will appreciate, some or all of the blocks in the workflow 1100 can overlap one another and can be repeated based on the results of other blocks. For example, the blocks 1112-1116 can overlap and be repeated a number of times. Some or all of the blocks in the workflow 1100 also can be performed by or facilitated by different tasked personnel at different stages of the workflow and for different states or status of the case record. For example, portions of some or all of blocks 1112-1116 can be performed or facilitated by different subsets of the tasked second personnel or by other additional teams or personnel.

The specific details of the specific aspects of implementations disclosed herein may be combined in any suitable manner without departing from the spirit and scope of the disclosed implementations. However, other implementations may be directed to specific implementations relating to each individual aspect, or specific combinations of these individual aspects. Additionally, while the disclosed examples are often described herein with reference to an implementation in which an on-demand database service environment is implemented in a system having an application server providing a front end for an on-demand database service capable of supporting multiple tenants, the present implementations are not limited to multi-tenant databases or deployment on application servers. Implementations may be practiced using other database architectures, i.e., ORACLE®, DB2® by IBM and the like without departing from the scope of the implementations claimed.

It should also be understood that some of the disclosed implementations can be embodied in the form of various types of hardware, software, firmware, or combinations thereof, including in the form of control logic, and using such hardware or software in a modular or integrated manner. Other ways or methods are possible using hardware and a combination of hardware and software. Additionally, any of the software components or functions described in this application can be implemented as software code to be executed by one or more processors using any suitable computer language such as, for example, Java, C++ or Perl using, for example, existing or object-oriented techniques. The software code can be stored as a computer- or processor-executable instructions or commands on a physical non-transitory computer-readable medium. Examples of suitable media include random access memory (RAM), read only memory (ROM), magnetic media such as a hard-drive or a floppy disk, or an optical medium such as a compact disk (CD) or DVD (digital versatile disk), flash memory, and the like, or any combination of such storage or transmission devices. Computer-readable media encoded with the software/program code may be packaged with a compatible device or provided separately from other devices (for example, via Internet download). Any such computer-readable medium may reside on or within a single computing device or an entire computer system, and may be among other computer-readable media within a system or network. A computer system, or other computing device, may include a monitor, printer, or other suitable display for providing any of the results mentioned herein to a user.

While some implementations have been described herein, it should be understood that they have been presented by way of example only, and not limitation. Thus, the breadth and scope of the present application should not be limited by any of the implementations described herein, but should be defined only in accordance with the following and later-submitted claims and their equivalents.

What is claimed is:

1. A system comprising:
    a database system implemented using a server system comprising one or more hardware processors, the database system configurable to cause:
        obtaining device data associated with a first device;
        analyzing the device data;
        detecting, based on the analysis, an occurrence of an exception associated with the first device;
        determining that a knowledge database storing one or more knowledge data objects identifying a plurality of prescriptions does not include a prescription applicable to the detected exception, each prescription of the plurality of prescriptions defining a respective action-oriented workflow for remedying one or more exceptions;

triggering, responsive to determining that the knowledge database does not include an applicable prescription, a plurality of different workflows, each workflow including, respectively:

tasking one or more designated persons to remedy the detected exception, and creating a troubleshooting data object configured to record actions performed by the one or more designated persons in attempting to remedy the detected exception;

performing an action analysis on actions recorded by the troubleshooting data object for one or more of the different workflows;

performing a correlative analysis on sets of actions recorded by the troubleshooting data object for the different workflows;

generating an automated script for remedying the detected exception based at least in part on both the action analysis and the correlative analysis; and creating a new prescription in the knowledge database, the new prescription identifying the automated script.

2. The system of claim 1, wherein the database system is further configurable to cause:
creating a case record for the detected exception.

3. The system of claim 2, wherein the database system is further configurable to cause:
updating a status of the case record based on the performance of one or more steps in a workflow.

4. The system of claim 1, wherein:
the new prescription includes a file, or a link to a file, that includes a software or firmware update; and
remedying the detected exception includes communicating the file to the first device for installation to the first device.

5. The system of claim 1, wherein
the different workflows include a first workflow and a second workflow.

6. The system of claim 1, wherein the database system is further configurable to cause:
analyzing activities recorded by other troubleshooting data objects; and
correlating results of the analysis of the activities recorded by the other troubleshooting data objects;
wherein the automated script for remedying the detected exception is further generated based on the analysis of the activities recorded by the other troubleshooting data objects and the correlation of the results.

7. The system of claim 1, wherein a workflow further includes identifying one or more second devices having one or more common characteristics with the first device and updating the second devices based on the new prescription.

8. A method for using a database system, the method comprising:
receiving device data associated with a first device;
analyzing the device data;
detecting, based on the analysis, an occurrence of an exception associated with the first device;
determining that a knowledge database storing one or more knowledge data objects identifying a plurality of prescriptions does not include a prescription applicable to the detected exception, each prescription of the plurality of prescriptions defining a respective action-oriented workflow for remedying one or more exceptions;

triggering, responsive to determining that the knowledge database does not include an applicable prescription, a plurality of different workflows, each workflow including, respectively:

tasking one or more designated persons to remedy the detected exception, and
creating a troubleshooting data object configured to record actions performed by the one or more designated persons in attempting to remedy the detected exception;

performing an action analysis on actions recorded by the troubleshooting data object for one or more of the different workflows;

performing a correlative analysis on sets of actions recorded by the troubleshooting data object for the different workflows;

generating an automated script for remedying the detected exception based at least in part on both the action analysis and the correlative analysis; and creating a new prescription in the knowledge database, the new prescription identifying the automated script.

9. The method of claim 8, further comprising:
creating a case record for the detected exception.

10. The method of claim 9, further comprising:
updating a status of the case record based on the performance of one or more steps in a workflow.

11. The method of claim 8, wherein:
the new prescription includes a file, or a link to a file, that includes a software or firmware update; and
remedying the detected exception includes communicating the file to the first device for installation to the first device.

12. The method of claim 8,
wherein the different workflows include a first workflow and a second workflow.

13. The method of claim 8, further comprising:
analyzing activities recorded by other troubleshooting data objects; and
correlating results of the analysis of the activities recorded by the other troubleshooting data objects;
wherein the automated script for remedying the detected exception is further generated based on the analysis of the activities recorded by the other troubleshooting data objects and the correlation of the results.

14. The method of claim 8, wherein a workflow further includes identifying one or more second devices having one or more common characteristics with the first device, and updating the second devices based on the new prescription.

15. A system comprising:
database system software stored on at least one non-transitory data storage medium for execution by at least one server of a database system, the database system software configurable to cause:
obtaining device data associated with a first device;
analyzing the device data;
detecting, based on the analysis, an occurrence of an exception associated with the first device;
determining that a knowledge database storing one or more knowledge data objects identifying a plurality of prescriptions does not include a prescription applicable to the detected exception, each prescription of the plurality of prescriptions defining a respective action-oriented workflow for remedying one or more exceptions;

triggering, responsive to determining that the knowledge database does not include an applicable prescription, a plurality of different workflows, each workflow including, respectively:
    tasking one or more designated persons to remedy the detected exception, and
    creating a troubleshooting data object configured to record actions performed by the one or more designated persons in attempting to remedy the detected exception;
performing an action analysis on actions recorded by the troubleshooting data object for one or more of the different workflows;
performing a correlative analysis on sets of actions recorded by the troubleshooting data object for the different workflows;
generating an automated script for remedying the detected exception based at least in part on both the action analysis and the correlative analysis; and
creating a new prescription in the knowledge database, the new prescription identifying the automated script.

16. The system of claim 15, wherein the different workflows include a first workflow and a second workflow.

17. The system of claim 15, wherein the database system software is further configurable to cause:
    creating a case record for the detected exception.

18. The system of claim 15, wherein:
    the new prescription includes a file, or a link to a file, that includes a software or firmware update; and
    remedying the detected exception includes communicating the file to the first device for installation to the first device.

19. The system of claim 15, wherein the database system software is further configurable to cause:
    analyzing activities recorded by other troubleshooting data objects; and
    correlating results of the analysis of the activities recorded by the other troubleshooting data objects;
wherein the automated script for remedying the detected exception is further generated based on the analysis of the activities recorded by the other troubleshooting data objects and the correlation of the results.

20. The system of claim 15, wherein a workflow further includes identifying one or more second devices having one or more common characteristics with the first device, and updating the second devices based on the new prescription.

* * * * *